US012649777B2

(12) United States Patent
Liu et al.

(10) Patent No.: US 12,649,777 B2
(45) Date of Patent: Jun. 9, 2026

(54) ANTIBODY FOR TETANUS TOXIN AND USE THEREOF

(71) Applicants: BEIJING WISDOMAB BIOTECHNOLOGY CO., LTD, Daxing District (CN); GENRIX (SHANGHAI) BIOPHARMACEUTICAL CO. LTD., Pudong District (CN); CHONGQING GENRIX BIOPHARMACEUTICAL CO., LTD., Chongqing (CN)

(72) Inventors: Zhigang Liu, Beijing (CN); Xiaowei Zhou, Beijing (CN); Yulan Liu, Beijing (CN); Xiaobo Hao, Beijing (CN); Junjie Hu, Beijing (CN)

(73) Assignees: BEIJING WISDOMAB BIOTECHNOLOGY CO., LTD, Daxing District (CN); GENRIX (SHANGHAI) BIOPHARMACEUTICAL CO. LTD., Pudong District (CN); CHONGQING GENRIX BIOPHARMACEUTICAL CO., LTD., Chongqing (CN)

( * ) Notice: Subject to any disclaimer, the term of this patent is extended or adjusted under 35 U.S.C. 154(b) by 601 days.

(21) Appl. No.: 18/033,006

(22) PCT Filed: Nov. 19, 2020

(86) PCT No.: PCT/CN2020/130111
§ 371 (c)(1),
(2) Date: Apr. 20, 2023

(87) PCT Pub. No.: WO2022/082918
PCT Pub. Date: Apr. 28, 2022

(65) Prior Publication Data
US 2025/0129141 A1 Apr. 24, 2025

(30) Foreign Application Priority Data
Oct. 21, 2020 (CN) .......................... 202011128926.0

(51) Int. Cl.
*C07K 16/1282* (2026.01)
*A61K 39/00* (2006.01)
*A61P 39/02* (2006.01)

(52) U.S. Cl.
CPC .......... *C07K 16/1282* (2013.01); *A61P 39/02* (2018.01); *A61K 2039/505* (2013.01); *C07K 2317/31* (2013.01); *C07K 2317/55* (2013.01); *C07K 2317/565* (2013.01); *C07K 2317/622* (2013.01); *C07K 2317/76* (2013.01); *C07K 2317/92* (2013.01)

(58) Field of Classification Search
CPC ................................................ A61K 47/6879
See application file for complete search history.

(56) References Cited

U.S. PATENT DOCUMENTS

| | | | |
|---|---|---|---|
| 4,816,567 | A | 3/1989 | Cabilly |
| 2001/0048922 | A1 | 12/2001 | Romet-Lemonne |
| 2003/0198595 | A1 | 10/2003 | Goldenberg |
| 2009/0155275 | A1 | 6/2009 | Wu |
| 2017/0327571 | A1 | 11/2017 | Liu |
| 2018/0169255 | A1 | 6/2018 | Changshou |
| 2020/0017595 | A1 | 1/2020 | Geuijen |
| 2020/0216540 | A1 | 7/2020 | Geuijen |
| 2020/0325227 | A1 | 10/2020 | Geuijen |
| 2020/0384084 | A1 | 12/2020 | Bakker |
| 2021/0340224 | A1 | 11/2021 | Liu |

FOREIGN PATENT DOCUMENTS

| | | | |
|---|---|---|---|
| CN | 1668335 | A | 9/2005 |
| CN | 101952312 | A | 1/2011 |
| CN | 102206275 | A | 10/2011 |
| CN | 102453091 | A | 5/2012 |
| CN | 105153305 | A | 12/2015 |
| CN | 106459205 | A | 2/2017 |
| CN | 108218984 | A | 6/2018 |
| CN | 108314730 | A | 7/2018 |
| CN | 108610417 | A | 10/2018 |
| CN | 108623681 | A | 10/2018 |
| CN | 109983033 | A | 7/2019 |
| CN | 110317267 | A | 10/2019 |
| CN | 111094347 | A | 5/2020 |
| CN | 111094350 | A | 5/2020 |

(Continued)

OTHER PUBLICATIONS

Vajdos et al. "Comprehensive Functional Maps of the Antigen-binding Site of an Anti-ErbB2 Antibody Obtained with Shotgun Scanning Mutagenesis", 2002, Journal of Molecular Biology, vol. 320, p. 415-428. (Year: 2002).*

MacCallum et al. "Antibody-antigen Interactions: Contact Analysis and Binding Site Topography", 1996, Journal of Molecular Biology, vol. 262, p. 732-745. (Year: 1996).*

Casset et al. "A peptide mimetic of an anti-CD4 monoclonal antibody by rational design" 2003, Biochemical and Biophysical Research Communications, vol. 307, p. 198-205. (Year: 2003).*

Xin et al. CN111116742A, published May 8, 2020—machine translated.*

Lu et al. (Jnl.Immunol. Meth., V267, 12, Sep. 15, 2002).*

(Continued)

*Primary Examiner* — Gary B Nickol

(74) *Attorney, Agent, or Firm* — NIXON PEABODY LLP; Bradley M. Taub; Nicole D. Kling

(57) ABSTRACT

Provided are a bispecific antibody and a monoclonal antibody for a tetanus toxin, and uses of the antibodies. The bispecific antibody contains a first antigen-binding fragment and a second antigen-binding fragment which bind to different epitopes of the tetanus toxin, and has activity of neutralizing the tetanus toxin. The monoclonal antibody binds to the tetanus toxin, and has activity of neutralizing the tetanus toxin.

13 Claims, 5 Drawing Sheets

Specification includes a Sequence Listing.

(56)               References Cited

FOREIGN PATENT DOCUMENTS

| | | | |
|---|---|---|---|
| CN | 111116742 | A | 5/2020 |
| CN | 111432838 | A | 7/2020 |
| CN | 111909265 | A | 11/2020 |
| CN | 111961136 | A | 11/2020 |
| WO | WO 2019/128119 | A1 | 7/2020 |
| WO | WO 2019/128120 | A1 | 7/2020 |

OTHER PUBLICATIONS

International Search Report and Written Opinion of International Searching Authority for International Patent Application No. PCT/CN2020/013011, mailed Jul. 21, 2021, with English translation of Search Report and Written Opinion (21 pages).

Lukic, I. et al.; "Cooperative binding of anti-tetanus toxin monoclonal antibodies: Implications for designing an efficient biclonal preparation to prevent tetanus toxin intoxication"; Vaccine, vol. 36, pp. 3764-3771; Dec. 31, 2018 (8 pages).

Huh, D.H. et al.; "Immunogenicity and protective efficacy of a newly developed tri-component diphtheria, tetanus, and acellular pertussis vaccine in a marine model"; Journal of Microbiology, Immunology and Infection, vol. 51, pp. 732-739; Jun. 29, 2017 (8pages).

Thwaites, C.L. et al.; "Maternal and neonatal tetanus"; Lancet 385:362-370; 2015; http://dx.doi.org/10.1016/50140-6736(14)60236-1 (9 pages).

Yousefi, M. et al.; "Characterization of neutralizing monoclonal antibodies directed against tetanus toxin fragment C"; J. Immunotoxicol. Early Online: 1-7; 2013 (7 pages).

Ashton, A.C. et al.; "Tetanus Toxin Inhibits Neuroexocytosis Even When Its Zn21+− Dependent Protease Activity is Removed"; J. Biol. Chem. Vol. 270, No. 52, pp. 31386-31390; Nov. 6, 1995 (6 pages).

Scott, N. et al.; "Characterisation of a panel of anti-tetanus toxin single-chain Fvs reveals cooperative binding"; Mol. Immunol. 47:1931-1941; Feb. 21, 2010 (11 pages).

Yousefi, M. et al.; "Comparative in vitro and in vivo assessment of toxin neutralization by anti-tetanus toxin monoclonal antibodies"; Hum. Vaccin. Immunother. 10:2, 344-351; Jan. 31, 2015 (9 pages).

Petrusic, V. et al.; "Production, characterization and applications of a tetanus toxin specific monoclonal antibody T-62"; Acta Histochem 114:480-486; 2012 (7 pages).

Lang, A.B. et al.; "Immunotherapy with human monoclonal antibodies. Fragment A specificity of polyclonal and monoclonal antibodies is crucial for full protection against tetanus toxin"; J. Immunol. vol. 151, No. 13, pp. 466-472; Jul. 1, 1993 (7 pages).

Merchant, A. M. et al.; "An efficient route to human bispecific IgG"; Nature Biotechnology, vol. 16, pp. 677-681; Jul. 1998 (5 pages).

Al-Lazikani et al.; "Standard Conformations for the Canonical Structures of Immunoglobulins"; J. Mol. Biol. vol. 273: 927-948 (1997) (22 pages).

Martin, A. et al.; "Modeling antibody hypervariable loops: A combined algorithm"; Proc. Natl. Acad. Sci. USA, vol. 86, pp. 9268-9272; Dec. 1989 (5 pages).

Krebber, A. et al.; "Reliable cloning of functional antibody variable domains from hybridomas and spleen cell repertoires employing a reengineered phage display system"; J. Immunol. Methods; 201, pp. 35-55; 1997 (21 pages).

Morrison, S. et al.; "Chimeric human antibody molecules: Mouse antigen-binding domains with human constant region domains"; Proc. Natl. Acad. Sci. USA, Immunology, vol. 81, pp. 6851-6855; Nov. 1984 (5 pages).

Tan, P. et al.; "'Superhumanized' antibodies: reduction of immunogenic potential by complementarity-determining region grafting with human germline sequences: application to an anti-CD28"; J. Immunol. 2002; 169:1119-1125 (8 pages).

Fanger, M. W. et al.; "Comments on the Fourth International Conference on Bispecific Antibodies and Cellular Cytotoxicity, Duck Key, Florida, Mar. 1-5, 1995"; J. Hematother., 4(5):345-349; 1995 (5 pages).

Han Wang et al.; "Tetanus Neurotoxin Neutralizing Antibodies Screened from a Human Immune scFv Antibody Phage Display Library"; Toxins (Basel), 8:266; Sep. 11, 2016; DOI: 10.3390/toxins8090266 (22 pages).

Volk, W. A. et al.; "Neutralization of Tetanus Toxin by Distinct Monoclonal Antibodies Binding to Multiple Epitopes on the Toxin Molecule"; Infection and Immunity, vol. 45, No. 3, pp. 604-509; American Society of Microbiology; Sep. 1984 (6 pages).

[Machine Translation] Answer on the grant of a patent for an invention and Search Report, by the Russian Federal Service for Intellectual Property, for International Application No. PCT/CN2020/130111 (9 pgs.); Dated Feb. 7, 2024.

[Machine Translation] Burkin et al., Determination of tetanus toxin and toxoid by ELISA using monoclonal antibodies. Applied Biochemistry and Microbiology 40 (2004): 409-414; Dated Mar. 28, 2024.

Chen et al.: "Purification and Immunogenicity Analysis of Tetanus Fragment C Expressed in *Escherichia coli*"; 2011 China Biological Products Annual Conference, pp. 192-195, with English Translation; Dec. 31, 2011 (11 pages).

Hong: "Neutralization of Tetanus Toxin by Distinct Monoclonal Antibodies Binding to Multiple Epitopes on the Toxin Molecule"; Foreign Medical Sciences, Section of Biologics for Prophylaxis, Diagnosis and Therapy, 1985 (with English Translation) (3 pages).

\* cited by examiner

ANTIBODY FOR TETANUS TOXIN AND USE THEREOF

CROSS REFERENCE TO RELATED APPLICATIONS

This application is a 35 U.S.C. § 371 National Phase Entry Applications of International Application No. PCT/CN2020/130111 filed Nov. 19, 2020, which designates the U.S. and claims benefit under 35 U.S.C. § 119(a) of Chinese Patent Application No. 202011128926.0 filed on Oct. 21, 2020, the contents of which are incorporated herein by reference in their entireties.

SEQUENCE LISTING

The instant application contains a Sequence Listing which has been submitted electronically in ASCII format and is hereby incorporated by reference in its entirety. Said ASCII copy, created on May 12, 2023, is named 078291-000308USPX_SL.txt and is 56,081 bytes in size.

TECHNICAL FIELD

The present application generally relates to the field of genetic engineering and antibody medicine. In particular, the present application relates to antibodies directed to a tetanus toxin and use thereof.

BACKGROUND

Tetanus is an acute and fetal disease caused by neurotoxins secreted by *Clostridium tetani*, and attacks humans and animals. The most susceptible animals are horses, mules, or donkeys from the order Perssodactyla. Humans are also susceptible to neurotoxins secreted by *Clostridium tetani*. This disease can be observed at any age. Neonatal tetanus is one of the main causes of neonatal death in economically underdeveloped areas. The incubation period of tetanus is generally 3-21 days, mostly about 10 days, but it may also be one day to several months depending on the characteristics, extent and location of the wound. Typical clinical manifestations of tetanus are teeth clenching, increased stress of motor nerve center, and local or systemic muscle spasmodic paralysis. Patients often die of asphyxia and systemic organ failure. Even with modern intensive cares, the mortality rate in this disease is very high. The mortality rate of tetanus can be 19% to 31% especially after severe natural disasters. There are three clinical types of tetanus, i.e., systemic tetanus, local tetanus and head tetanus, which account for about 88%, about 12%, and about 1% resepetively in all cases.

*Clostridium tetani* is a strict anaerobic, gram-positive bacterium. It has flagella but no capsule. Its spores are widely found in fertilized soil, street dust, rancid sludge, animal intestines, and contaminated object surfaces. *Clostridium tetani* enters the human body mainly through a wound. If the wound is narrow and deep, or if the wound is simultaneously infected with aerobic pyogenic bacteria, *Clostridium tetani* will multiply in large number under anaerobic conditions and produce three exotoxins, among which the tetanus toxin causes characteristic symptoms of tetanus and elicits the production of protective antibodies [1]. However, about 20% of patients have no apparent invasive wounds, suggesting that *Clostridium tetani* can also invade the body through small scratch surfaces. *Clostridium tetani* can be divided into ten serotypes according to the agglutination reactions of flagellar antigen, but all serotypes produce the same neurotoxin. The toxins produced by individual types of strains can be neutralized by any type of antitoxin. The tetanus toxin is highly toxic, second only to botulinum toxin. Its lethal dose to mice is only 2-6 ng/kg.

The tetanus toxin, also known as the tetanus neurotoxin, is a single chain protein, which has a relative molecular weight of about 150 kDa, consists of 1315 amino acid residues, and can be cleaved into a light chain (fragment A, 50 kDa) and a heavy chain (HC, 100 kDa) linked via a disulfide bond, thereby forming its active form [2]. Fragment A is a zinc metalloproteinase that, upon entry into the cytoplasm, digests vesicle-associated membrane protein-2 (VAMP-2) and blocks the release of inhibitory neurotransmitters such as glycine and gamma-aminobutyric acid (GABA), resulting in muscle spasmodic paralysis [3]. The heavy chain comprises two functional domains. The C-terminal domain (Fragment C) binds to the surfaces of nerve cells such that the toxin molecule is endocytosed into vesicles. The N-terminal domain (Fragment B) passes the vesicle membrane and transports Fragment A into the neuronal cytoplasm [4]. Fragment C is subdivided into C-terminal subdomain (HCC) and N-terminal subdomain (HCN) [5]. The process by which the tetanus toxin enters neural cells is not fully understood. At present, a dual receptor mechanism is generally accepted, and involves a ganglioside receptor, in particular GT1b and GD1b, and a protein receptor [6].

Tetanus is a preventable disease. Subjects can receive active and passive immunization treatment after trauma. Humoral immunity has a protective effect on tetanus. Neutralizing antibodies bind to the toxin, and interfere with the interaction of the toxin with receptors on target cells and subsequent internalization of the toxin into the cell. Clinically, passive immunization is recommended for trauma patients who have unclear immunization history or are not immunized, have not received complete prime immunization, or have received complete prime immunization but with the last boost immunization received more than 5 years ago. Currently, there are two kinds of passive immune preparations for the prevention and treatment of tetanus in clinic. One is tetanus antitoxin (TAT), which is made from horse plasma immunized with tetanus toxoid by enzymatic digestion and salting-out. Before use of TAT, a skin test is required. TAT often causes allergic reactions with the incidence being 5%-30%. Anaphylactic shock occasionally occurs. The other kind of passive immune preparations is human immunoglobulin for tetanus (HIGT), which is made by taking plasma or serum with high titer of tetanus antibody from blood donors successively immunized with hepatitis B vaccine and tetanus toxoid, and processing the plasma or serum using the low temperature ethanol method. HIGT can be injected directly without skin test. However, as HIGT belongs to blood preparations, there is a potential risk of infectious diseases such as hepatitis C and AIDS. In addition, HIGT is limited by sources, and has low output, high cost and inconsistent quality among batches. [7]

Antibody drugs can overcome some of the above shortcomings and have certain advantages, such as production by stable expression by mammal cell expression systems, and definite composition.

Due to clinical needs, it is of great medical significance to develop antibodies that can neutralize the tetanus toxin and be used in preventing and treating tetanus.

SUMMARY OF THE INVENTION

In a first aspect, there is provided in the present application a bispecific antibody comprising a first antigen-binding fragment and a second antigen-binding fragment that bind different epitopes of a tetanus toxin, wherein the bispecific antibody has activity of neutralizing the tetanus toxin.

In some embodiments of the first aspect, the first antigen-binding fragment comprises HCDR1 having the amino acid sequence of SYWIY (SEQ ID NO: 1), HCDR2 having the amino acid sequence of EINPTNGFANYNEKFKT (SEQ ID NO: 2) or EINPTAGFANYNEKFKT (SEQ ID NO: 3) or EINPTNAFANYNEKFKT (SEQ ID NO: 4), HCDR3 having the amino acid sequence of HFRFPY (SEQ ID NO: 5), LCDR1 having the amino acid sequence of RASQDIGSSLT (SEQ ID NO: 6), LCDR2 having the amino acid sequence of ATSSLDS (SEQ ID NO: 7) and LCDR3 having the amino acid sequence of LQYASSPYT (SEQ ID NO: 8); wherein the HCDR and LCDR amino acid sequences are defined according to Kabat.

In some embodiments of the first aspect, the second antigen-binding fragment comprises HCDR1 having the amino acid sequence of DYGVN (SEQ ID NO: 9), HCDR2 having the amino acid sequence of MIWSDGTTDYS-SALKS (SEQ ID NO: 10), HCDR3 having the amino acid sequence of VDGYSHYYAMDY (SEQ ID NO: 11), LCDR1 having the amino acid sequence of RASENIY-SYLA (SEQ ID NO: 12), LCDR2 having the amino acid sequence of NAKTLAE (SEQ ID NO: 13) and LCDR3 having the amino acid sequence of QHHYGLPFT (SEQ ID NO: 14); wherein the HCDR and LCDR amino acid sequences are defined according to Kabat.

In some embodiments of the first aspect, the amino acid sequence of the heavy chain variable region of the first antigen-binding fragment is as set forth in SEQ ID NO: 15, and the amino acid sequence of the light chain variable region of the first antigen-binding fragment is as set forth in SEQ ID NO: 18; or the amino acid sequence of the heavy chain variable region of the first antigen-binding fragment is as shown in SEQ ID NO: 16, and the amino acid sequence of the light chain variable region of the first antigen-binding fragment is as shown in SEQ ID NO: 18; or the amino acid sequence of the heavy chain variable region of the first antigen-binding fragment is as set forth in SEQ ID NO: 17, and the amino acid sequence of the light chain variable region of the first antigen-binding fragment is as set forth in SEQ ID NO: 18.

In some embodiments of the first aspect, the amino acid sequence of the heavy chain variable region of the second antigen-binding fragment is as set forth in SEQ ID NO: 19, and the amino acid sequence of the light chain variable region of the second antigen-binding fragment is as set forth in SEQ ID NO: 20.

In some embodiments of the first aspect, the forms of the first antigen-binding fragment and the second antigen-binding fragment are independently selected from a single-chain fragment variable (scFv) or a Fab fragment.

In a second aspect, there is provided in the application a monoclonal antibody that binds to a tetanus toxin, comprising:

HCDR1 having the amino acid sequence of SYWIY (SEQ ID NO: 1), HCDR2 having the amino acid sequence of EINPTNGFANYNEKFKT (SEQ ID NO: 2) or EINPTAGFANYNEKFKT (SEQ ID NO: 3) or EINPT-NAFANYNEKFKT (SEQ ID NO: 4), HCDR3 having the amino acid sequence of HFRFPY (SEQ ID NO: 5), LCDR1 having the amino acid sequence of RASQ-DIGSSLT (SEQ ID NO: 6), LCDR2 having the amino acid sequence of ATSSLDS (SEQ ID NO: 7) and LCDR3 having the amino acid sequence of LQYASSPYT (SEQ ID NO: 8); wherein the HCDR and LCDR amino acid sequences are defined according to Kabat.

In a third aspect, there is provided in the application a monoclonal antibody that binds to a tetanus toxin, comprising:

HCDR1 having the amino acid sequence of DYGVN (SEQ ID NO: 9), HCDR2 having the amino acid sequence of MIWSDGTTDYSSALKS (SEQ ID NO: 10), HCDR3 having the amino acid sequence of VDGYSHYYAMDY (SEQ ID NO: 11), LCDR1 having the amino acid sequence of RASENIYSYLA (SEQ ID NO: 12), LCDR2 having the amino acid sequence of NAKTLAE (SEQ ID NO: 13), and LCDR3 having the amino acid sequence of QHHYGLPFT (SEQ ID NO: 14); wherein the HCDR and LCDR amino acid sequences are defined according to Kabat.

In a fourth aspect, there is provided in the application a pharmaceutical composition comprising the bispecific antibody of the first aspect, or the monoclonal antibody of the second or third aspect, and a pharmaceutically acceptable excipient, diluent, or carrier.

In a fifth aspect, there is provided in the application use of the bispecific antibody of the first aspect, the monoclonal antibody of the second or third aspect, or the pharmaceutical composition of the fourth aspect in the manufacture of a medicament for the prevention or treatment of tetanus.

DESCRIPTION OF THE SEQUENCES

Figure 1:
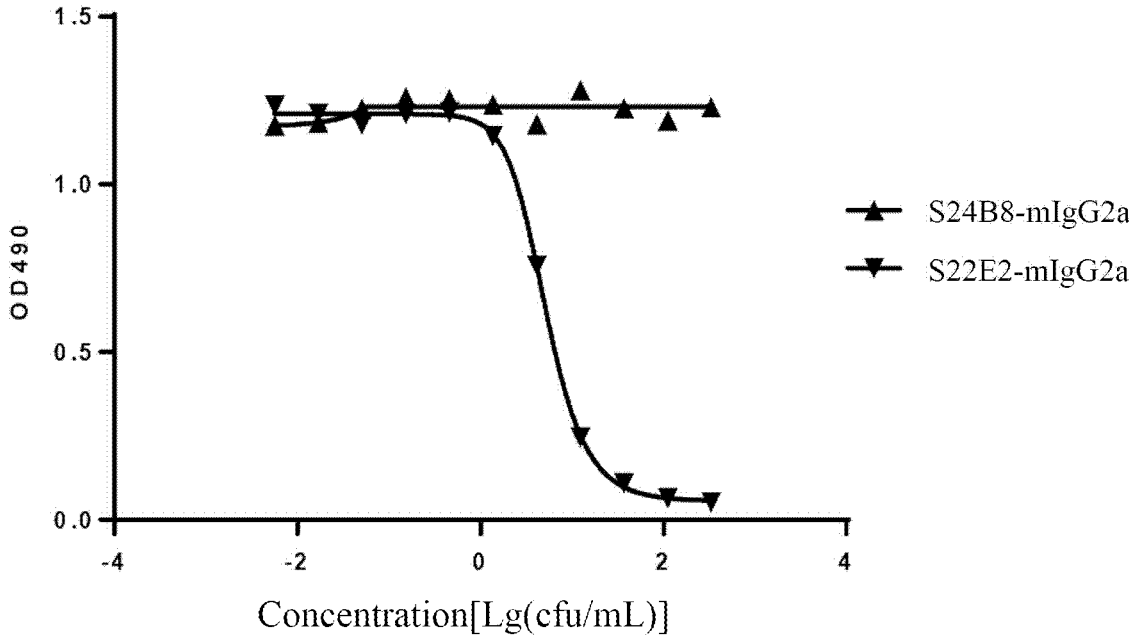
FIG. 1 shows the results from an ELISA assay assessing how anti-TT-Hc monoclonal antibodies S22E2-mIgG2a and S24B8-mIgG2a inhibit binding of S22E2 purified phage to TT-Hc.

SEQ ID NO: 1 shows the amino acid sequence of HCDR1 of the humanized heavy chain variable region mutants S24B8VH-h1, S24B8VH-h2 and S24B8VH-h3.

SEQ ID NO: 2 shows the amino acid sequence of HCDR2 of the humanized heavy chain variable region mutant S24B8VH-h1.

SEQ ID NO: 3 shows the amino acid sequence of HCDR2 of the humanized heavy chain variable region mutant S24B8VH-h2.

SEQ ID NO: 4 shows the amino acid sequence of HCDR2 of the humanized heavy chain variable region mutant S24B8VH-h3.

SEQ ID NO: 5 shows the amino acid sequence of HCDR3 of the humanized heavy chain variable region mutants S24B8VH-h1, S24B8VH-h2 and S24B8VH-h3.

SEQ ID NOs: 6-8 show the amino acid sequences of LCDR1, LCDR2 and LCDR3 of the humanized light chain variable region mutant S24B8VK-h1, respectively.

SEQ ID NOs: 9-11 show the amino acid sequences of HCDR1, HCDR2 and HCDR3 of the humanized heavy chain variable region mutant S22E2VH-h1, respectively.

SEQ ID NOs: 12-14 show the amino acid sequences of LCDR1, LCDR2 and LCDR3 of the humanized light chain variable region mutant S22E2VK-h1, respectively.

SEQ ID NO: 15 shows the amino acid sequence of the humanized heavy chain variable region mutant S24B8VH-h1.

SEQ ID NO: 16 shows the amino acid sequence of the humanized heavy chain variable region mutant S24B8VH-h2.

SEQ ID NO: 17 shows the amino acid sequence of the humanized heavy chain variable region mutant S24B8VH-h3.

SEQ ID NO: 18 shows the amino acid sequence of the humanized light chain variable region mutant S24B8VK-h1.

SEQ ID NO: 19 shows the amino acid sequence of the humanized heavy chain variable region mutant S22E2VH-h1.

SEQ ID NO: 20 shows the amino acid sequence of the humanized light chain variable region mutant S22E2VK-h1.

SEQ ID NO: 21 shows the amino acid sequence of S24B8VH-h1+CH-IgG1K.

SEQ ID NO: 22 shows the amino acid sequence of S24B8VH-h2+CH-IgG1K.

SEQ ID NO: 23 shows the amino acid sequence of S24B8VH-h3+CH-IgG1K.

SEQ ID NO: 24 shows the amino acid sequence of S24B8VK-h1+CK.

SEQ ID NO: 25 shows the amino acid sequence of S22E2-h1-scFv-FcH1.

SEQ ID NO: 26 shows the amino acid sequence of the C-terminal domain recombinant protein (TT-Hc) of the tetanus toxin heavy chain.

SEQ ID NO: 27 shows the amino acid sequence of the His tag.

SEQ ID NO: 28 shows the amino acid sequence of human (*Homo sapiens*) IgG1 subtype heavy chain constant region.

SEQ ID NO: 29 shows the amino acid sequence of murine (*Mus musculus*) IgG2a subtype heavy chain constant region.

SEQ ID NO: 30 shows the amino acid sequence of human IgG1 subtype mutant IgG1H.

SEQ ID NO: 31 shows the amino acid sequence of human IgG1 subtype mutant IgG1K.

SEQ ID NO: 32 shows the amino acid sequence of murine IgG2a subtype mutant mIgG2a-H.

SEQ ID NO: 33 shows the amino acid sequence of murine IgG2a subtype mutant mIgG2aK.

SEQ ID NO: 34 shows the amino acid sequence of human (*Homo sapiens*) kappa subtype light chain constant region.

SEQ ID NO: 35 shows the amino acid sequence of human (*Homo sapiens*) lamda subtype light chain constant region.

SEQ ID NO: 36 shows the amino acid sequence of murine (*Mus musculus*) kappa subtype light chain constant region.

SEQ ID NO: 37 shows the amino acid sequence of murine (*Mus musculus*) lamda subtype light chain constant region.

SEQ ID NO: 38 shows the nucleotide sequence of primer PmCGR.

SEQ ID NO: 39 shows the nucleotide sequence of primer PmCKR.

SEQ ID NO: 40 shows the amino acid sequence of the Fc segment containing the Knob mutation (FcK).

SEQ ID NO: 41 shows the amino acid sequence of the Fc segment containing the Hole mutation (FcH1).

DETAILED DESCRIPTION OF THE INVENTION

The inventors of the present application conducted extensive research and development of antibody drugs against tetanus, and obtained novel bispecific antibodies and monoclonal antibodies against the tetanus toxin by antibody engineering techniques. The tetanus toxin is a macromolecular protein which consists of several domains. Theoretically, its has many epitopes that can elicits humoral immunity, and antibodies that bind to different epitopes can be obtained from immunized subjects. Fragment C of the tetanus toxin is a receptor-binding domain and it is likely that antibodies against Fragment C have neutralization activies by preventing the toxin from binding to gangliosides GT1b, GD1b and GM1, and achieving neutralizing effects on the toxin.

In various aspects of the present application, there are provided novel bispecific antibodies and mononal antibodies against the tetanus toxin, polynucleotides encoding the bispecific antibodies or mononal antibodies, vectors comprising the polynucleotides, host cells comprising the polynucleotides or vectors, methods of preparing and purifying the bispecific antibodies or mononal antibodies, and medical and biological use of the bispecific antibodies or mononal antibodies. Based on the sequences of the variable regions of the bispecific antibodies or mononal antibodies provided herein, full-length bispecific antibody molecules or mononal antibody molecules can be constructed for clinical use as a medicament for preventing or treating tetanus.

Unless otherwise indicated, the inventions of the present application can be practiced using conventional molecular biology, microbiology, cell biology, biochemistry, and immunological techniques in the art.

Unless otherwise indicated, the terms used in the present application have the meanings commonly understood by those skilled in the art.

Definitions

As used herein, the term "antibody" refers to an immunoglobulin molecule that is capable of specifically binding to a target via at least one antigen recognition site located in a variable region of the immunoglobulin molecule. Targets include, but are not limited to, carbohydrates, polynucleotides, lipids, and polypeptides. As used herein, an "antibody" includes not only an intact (i.e., full-length) antibody, but also an antigen-binding fragment thereof (e.g., Fab, Fab', F(ab')₂, Fv), a variant thereof, a fusion protein comprising portions of an antibody, a humanized antibody, a chimeric antibody, a diabody, a linear antibody, a single-chain antibody, a multi-specific antibody (e.g., a bispecific antibody), and any other modified formats of an immunoglobulin molecule comprising a desired specific antigen recognition site, including a glycosylated variant of an antibody, an amino acid sequence variant of an antibody, and a covalently modified antibody.

Typically, an intact or full-length antibody comprises two heavy chains and two light chains. Each heavy chain contains a heavy chain variable region (VH) and first, second and third constant regions (CH1, CH2 and CH3). Each light chain contains a light chain variable region (VL) and a constant region (CL). A full-length antibody may be of any type, such as an IgD, IgE, IgG, IgA, or IgM (or their subtypes) antibody, but not necessarily belong to any particular type. Immunoglobulins can be assigned to different types depending on their amino acid sequences of the heavy chain constant domains. Generally, immunoglobulins have five main types, i.e., IgA, IgD, IgE, IgG, and IgM, and some of these types can be further classified into subtypes (isotypes), such as IgG1, IgG2, IgG3, IgG4, IgA1, and IgA2. Heavy chain constant domains corresponding to individual immunoglobulin types are referred to as α, δ, ε, γ, and μ, respectively. Subunit structures and three-dimensional structures of different types of immunoglobulins are well known.

As used herein, the term "bispecific antibody" is an antibody having the ability to bind to two different antigens. A bispecific antibody can have a variety of structural configurations. For example, a bispecific antibody may consist of two Fc fragments and two antigen-binding portions fused thereto, respectively (similar to a natural antibody, except that the two arms bind to different antigen targets or epitopes). Antigen-binding portions can be in the form of scfv or Fab fragments. When two antigens are given, two different antigen-binding portions of a bispecific antibody each binds to the N-terminus of one Fc fragment. The configuration of the antigen-binding portions of the two arms can have the four combinations, i.e., scfv+Fab fragment, Fab fragment +scfv, scfv+scfv, and Fab fragment+Fab fragment. Fc fragments can contain mutations that can ensure heavy chain heteromerization. The KIH (knob-in-hole) technique is one strategy to address heavy chain heteromerization. Generally, the KIH technique refers to formation of a structure that facilitates the pairing of heterogeneous hemibodies by engineering the amino acid sequence of a CH3 region. This can maintain the structure of a normal antibody as much as possible while forming a bispecific antibody. For guidance of the KIH technique, see, for example, "An efficient route to human bispecific IgG", A. Margaret Merchant et al., Nature Biotechnology, Volume 16, 1998, which is incorporated herein by reference in its entirety. Furthermore, a bispecific antibody can be configured in a way that an antibody that binds to a first antigen (e.g., in the form of a natural antibody) has an antigen-binding portion that can bind to a second antigen extending from the C-terminus of the $CH_3$ region (e.g., via a flexible linker).

As used herein, the term "antigen-binding portion" or "antigen-binding fragment" can be used interchangeably, and refers to a portion or region of an intact antibody molecule responsible for binding to an antigen. An antigen binding domain can comprise a heavy chain variable region (VH), a light chain variable region (VL), or both. Each of a VH and a VL typically contains three complementarity determining regions, i.e., CDR1, CDR2, and CDR3.

It is well known to those skilled in the art that complementarity determining regions (CDRs, usually including CDR1, CDR2 and CDR3) are the regions of a variable region that have mostly impact on the affinity and specificity of an antibody. The CDR sequences of a VH or VL have two common definitions, i.e., the Kabat definition and the Chothia definition (see, e.g., Kabat, "Sequences of Proteins of Immunological Interest", National Institutes of Health, Bethesda, Md.(1991); Al-Lazikani et al., J. Mol. Biol. 273:927-948 (1997); and Martin et al., Proc. Natl. Acad. Sci. USA 86: 9268-9272 (1989)). For the variable region sequences of a given antibody, the sequences of CDR regions in the VH and VL can be determined according to the Kabat definition or the Chothia definition. In an embodiment of the present application, CDR sequences are defined according to Kabat.

For the variable region sequences of a given antibody, the sequences of CDR regions in the variable region sequences can be analyzed in a variety of ways, for example, using online software Abysis (http://www.abysis.org/).

For conventional antibodies, examples of an antigen-binding fragment include, but are not limited to, (1) an Fab fragment, which can be a monovalent fragment having a VL-CL chain and a VH-CH1 chain; (2) an $F(ab')_2$ fragment, which can be a divalent fragment having two Fab' fragments linked by a disulfide bridge of the hinge region (i.e., a dimer of Fab'); (3) an Fv fragment having VL and VH domains in a single arm of an antibody; (4) a single chain Fv (scFv), which can be a single polypeptide chain consisting of a VH domain and a VL domain via a polypeptide linker; and (5) $(scFv)_2$, which can comprise two VH domains linked by a peptide linker and two VL domains that are combined with the two VH domains via a disulfide bridge.

In bispecific antibody construction, an "antigen-binding portion" includes, but is not limited to, a Fab fragment or a single-chain fragment variable (scFv).

As used herein, the term "single chain fragment variable (scFv)" refers to an antibody of a single chain structure generally constructed using genetic engineering techniques, comprising a polypeptide chain comprising a heavy chain variable region (VH) and a light chain variable region (VL). A flexible linker is typically designed between the heavy chain variable region and the light chain variable region so that the heavy chain variable region and the light chain variable region can be folded into the correct conformation for binding to an antigen.

As used herein, the term "Fab (fragment antigen-binding) fragment", "Fab portion", or the like refers to an antibody fragment that is produced after treatment of an intact antibody with papain and is capable of binding to an antigen, including the intact light chain (VL-CL), the heavy chain variable region, and the CH1 fragment (VH-CH1).

As used herein, the term "monoclonal antibody" refers to an antibody from a substantially homogeneous antibody population, which means that the antibodies constituting the population are the same except for naturally occurring mutations which may occur in a small number of individual antibodies. Monoclonal antibodies described herein particularly include "chimeric" antibodies in which a portion of the heavy and/or light chain is identical or homologous to a corresponding sequence in an antibody derived from a particular species or belonging to a particular antibody type or subtype, while the remainder of the heavy and/or light chain is identical or homologous to a corresponding sequence in an antibody derived from another species or belonging to another antibody type or subtype, and also include fragments of such antibodies as long as they exhibit desired biological activity (see, U.S. Pat. No. 4,816,567; and Morrison et al., Proc. Natl. Acad. Sci. USA 81: 6851-6855 (1984)).

As used herein, the term "specific binding" refers to a non-random binding reaction between two molecules, e.g., binding of an antibody to an antigen epitope.

In a first aspect, there is provided in the present application a bispecific antibody comprising a first antigen-binding fragment and a second antigen-binding fragment that bind to different epitopes of a tetanus toxin, wherein the bispecific antibody has activity of neutralizing the tetanus toxin.

In some embodiments of the first aspect, the first antigen-binding fragment comprises HCDR1 having the amino acid sequence of SYWIY (SEQ ID NO: 1), HCDR2 having the amino acid sequence of EINPTNGFANYNEKFKT (SEQ ID NO: 2) or EINPTAGFANYNEKFKT (SEQ ID NO: 3) or EINPTNAFANYNEKFKT (SEQ ID NO: 4), HCDR3 having the amino acid sequence of HFRFPY (SEQ ID NO: 5), LCDR1 having the amino acid sequence of RASQDIGSSLT (SEQ ID NO: 6), LCDR2 having the amino acid sequence of ATSSLDS (SEQ ID NO: 7) and LCDR3 having the amino acid sequence of LQYASSPYT (SEQ ID NO: 8); wherein the HCDR and LCDR amino acid sequences are defined according to Kabat.

In some embodiments of the first aspect, the second antigen-binding fragment comprises HCDR1 having the amino acid sequence of DYGVN (SEQ ID NO: 9), HCDR2 having the amino acid sequence of MIWSDGTTDYS-SALKS (SEQ ID NO: 10), HCDR3 having the amino acid sequence of VDGYSHYYAMDY (SEQ ID NO: 11), LCDR1 having the amino acid sequence of RASENIY-SYLA (SEQ ID NO: 12), LCDR2 having the amino acid sequence of NAKTLAE (SEQ ID NO: 13) and LCDR3 having the amino acid sequence of QHHYGLPFT (SEQ ID NO: 14); wherein the HCDR and LCDR amino acid sequences are defined according to Kabat.

In some embodiments of the first aspect, the amino acid sequence of the heavy chain variable region of the first antigen-binding fragment is as set forth in SEQ ID NO: 15, and the amino acid sequence of the light chain variable region is as set forth in SEQ ID NO: 18; or the amino acid sequence of the heavy chain variable region of the first antigen-binding fragment is as shown in SEQ ID NO: 16, and the amino acid sequence of the light chain variable region of the first antigen-binding fragment is as shown in SEQ ID NO: 18; or the amino acid sequence of the heavy chain variable region of the first antigen-binding fragment is as set forth in SEQ ID NO: 17, and the amino acid sequence of the light chain variable region of the first antigen-binding fragment is as set forth in SEQ ID NO: 18.

In some embodiments of the first aspect, the amino acid sequence of the heavy chain variable region of the second antigen-binding fragment is as set forth in SEQ ID NO: 19, and the amino acid sequence of the light chain variable region of the second antigen-binding fragment is as set forth in SEQ ID NO: 20.

In some embodiments of the first aspect, the forms of the first antigen-binding fragment and the second antigen-binding fragment are independently selected from a single-chain fragment variable (scFv) or a Fab fragment.

In some embodiments of the first aspect, the first antigen-binding fragment is a Fab fragment, and the second antigen-binding fragment is a single-chain fragment variable (scFv).

In some embodiments of the first aspect, the bispecific antibody comprises the amino acid sequence set forth in one of SEQ ID NOs: 21, 22, and 23 and the amino acid sequence set forth in SEQ ID NO: 24.

In some embodiments of the first aspect, the bispecific antibody comprises the amino acid sequence set forth in SEQ ID NO: 25.

In a second aspect, there is provided in the application a monoclonal antibody that binds to a tetanus toxin, comprising:

HCDR1 having the amino acid sequence of SYWIY (SEQ ID NO: 1), HCDR2 having the amino acid sequence of EINPTNGFANYNEKFKT (SEQ ID NO: 2) or EINPTAGFANYNEKFKT (SEQ ID NO: 3) or EINPT-NAFANYNEKFKT (SEQ ID NO: 4), HCDR3 having the amino acid sequence of HFRFPY (SEQ ID NO: 5), LCDR1 having the amino acid sequence of RASQ-DIGSSLT (SEQ ID NO: 6), LCDR2 having the amino acid sequence of ATSSLDS (SEQ ID NO: 7) and LCDR3 having the amino acid sequence of LQYASSPYT (SEQ ID NO: 8); wherein the HCDR and LCDR amino acid sequences are defined according to Kabat.

In some embodiments of the second aspect, the monoclonal antibody comprises a heavy chain variable region amino acid sequence set forth in SEQ ID NO: 15, and a light chain variable region amino acid sequence set forth in SEQ ID NO: 18; or a heavy chain variable region amino acid sequence set forth in SEQ ID NO: 16, and a light chain variable region amino acid sequence set forth in SEQ ID NO: 18; or a heavy chain variable region amino acid sequence set forth in SEQ ID NO: 17, and a light chain variable region amino acid sequence set forth in SEQ ID NO: 18.

In a third aspect, there is provided in the application a monoclonal antibody that binds to a tetanus toxin, comprising:

HCDR1 having the amino acid sequence of DYGVN (SEQ ID NO: 9), HCDR2 having the amino acid sequence of MIWSDGTTDYSSALKS (SEQ ID NO: 10), HCDR3 having the amino acid sequence of VDGYSHYYAMDY (SEQ ID NO: 11), LCDR1 having the amino acid sequence of RASENIYSYLA (SEQ ID NO: 12), LCDR2 having the amino acid sequence of NAKTLAE (SEQ ID NO: 13), and LCDR3 having the amino acid sequence of QHHYGLPFT (SEQ ID NO: 14); wherein the amino acid sequences of HCDR and LCDR are defined according to Kabat.

In some embodiments of the third aspect, the monoclonal antibody comprises a heavy chain variable region amino acid sequence set forth in SEQ ID NO: 19, and a light chain variable region amino acid sequence set forth in SEQ ID NO: 20.

In a fourth aspect, there is provided in the application a pharmaceutical composition comprising the bispecific antibody of the first aspect, or the monoclonal antibody of the second or third aspect, and a pharmaceutically acceptable excipient, diluent, or carrier.

In some embodiments of the fourth aspect, the pharmaceutical composition is for preventing or treating tetanus.

In some embodiments of the fourth aspect, the pharmaceutical composition may further comprise one or more of a lubricant, such as talc, magnesium stearate, and mineral oil; a wetting agent; an emulsifier; a suspending agent; a preservative such as benzoic acid, sorbic acid and calcium propionate; a sweetening agent and/or a flavoring agent.

In some embodiments of the fourth aspect, the pharmaceutical composition herein may be formulated as a tablet, a pill, a powder, a lozenge, an elixir, a suspension, an emulsion, a solution, a syrup, a suppository, or a capsule.

In some embodiments of the fourth aspect, the pharmaceutical composition of the present application may be delivered using any physiologically acceptable administration route including, but not limited to, oral administration, parenteral administration, nasal administration, rectal administration, intraperitoneal administration, intravascular injection, subcutaneous administration, transdermal administration, or inhalation administration.

In some embodiments of the fourth aspect, a pharmaceutical composition for therapeutic use may be formulated for storage in a lyophilized formulation or in the form of an aqueous solution by mixing an agent with desired purity with a pharmaceutically acceptable carrier or excipient where appropriate.

In a fifth aspect, there is provided in the application use of the bispecific antibody of the first aspect, the monoclonal antibody of the second or third aspect, or the pharmaceutical composition of the fourth aspect in the manufacture of a medicament for the prevention or treatment of tetanus.

In a sixth aspect, there is provided in the application a method of preventing or treating tetanus, comprising administering to a subject in need thereof the bispecific antibody of the first aspect, the monoclonal antibody of the second or third aspect, or the pharmaceutical composition of the fourth aspect.

In other aspects, there is provided in the application a nucleic acid molecule encoding the bispecific antibody of the first aspect, or the monoclonal antibody of the second or third aspect. In some embodiments, the nucleic acid molecule is operably linked to a regulatory sequence that can be recognized by a host cell transformed with the vector.

There is also provided in the application a vector comprising an isolated nucleic acid molecule encoding the bispecific antibody of the first aspect, or the monoclonal antibody of the second or third aspect, and a host cell comprising the nucleic acid molecule or the vector.

In other aspects, there is provided in the application a method of producing the bispecific antibody of the first aspect, or the monoclonal antibody of the second or third aspect. In some embodiments, the method of producing the bispecific antibody of the first aspect, or the monoclonal antibody of the second or third aspect comprises culturing a host cell so as to facilitate expression of the nucleic acid. In some embodiments, the method of producing the bispecific antibody of the first aspect, or the monoclonal antibody of the second or third aspect further comprises recovering the bispecific antibody or monoclonal antibody from the host cell culture medium.

It is to be understood that the foregoing detailed description is intended only to enable those skilled in the art to have better understanding of the present application and is not intended to cause limitations in any way. Various modifications and variations can be made to the described embodiments by those skilled in the art.

The following Examples are for purposes of illustration only and are not intended to limit the scope of the present application.

EXAMPLES

Example 1: Preparation of Recombinant Tetanus Toxin Antigen and Recombinant Antibodies

1.1 Preparation of Recombinant Tetanus Toxin Antigen

A recombinant protein of C-terminal domain of tetanus toxin heavy chain (TT-Hc, SEQ ID NO:26) was used in the production of monoclonal antibodies against tetanus toxin. This protein was derived from *Clostridium tetani* and was lack of any post-translational modification, and therefore can be expressed using an *E. coli* expression system. Furthermore, an His tag (His, SEQ ID NO:27) was added to the C-terminus of the recombinant protein, so as to facilitate the purification of the recombinant protein and the identification of the function of the monoclonal antibody.

A gene encoding TT-Hc (containing the His tag) was designed and synthesized according to the amino acid sequences of the TT-Hc recombinant proteins in the Uniprot database. The synthesized gene was cloned into a suitable eukaryotic expression vector (such as pET-22b, Invitrogen, Inc.) using conventional molecular biology techniques. Expression plasmids were transformed into competent *E. coli* cells (such as BL21 (DE3), Solarbio, Inc.). The *E. coli* expressing the TT-Hc-His recombinant protein was induced to express by IPTG (such as 18070-1g, Solarbio, Inc.). Then, the bacteria were collected by centrifugation and disrupted by an ultrasonic cell crusher (such as VCX130, Sonics, Inc.). The supernatants were harvested by centrifugation. The recombinant protein in the supernatants was further purified by a metal-chelated affinity chromatography column (such as HisTrap FF, GE, Inc.). The recombinant protein preservation buffer was then replaced with PBS (pH 7.0) or other suitable buffers by using a desalting column (such as Hitrap desalting, GE, Inc.). If necessary, the sample can be sterilized by filtration and then stored in aliquots at −20° C.

1.2. Preparation of Recombinant Antibodies

Nucleotide sequences encoding the antibody heavy chain variable region and light chain variable region were cloned into eukaryotic expression vectors (such as pcDNA3.1, Invitrogen, Inc.) carrying the nucleotide sequences encoding the heavy chain constant region and the light chain constant region, respectively, using conventional molecular biological means. Intact antibodies were expressed in combination. The heavy chain constant regions of antibodies can be of human IgG1 subtype (SEQ ID NO: 28), or murine IgG2a subtype (SEQ ID NO: 29), or can be human IgG1 subtype mutant IgG1H (SEQ ID NO: 30) and IgG1K (SEQ ID NO: 31) based on the KIH (Knob-Into-Hole) technology, or can be murine IgG2a subtype mutant mIgG2a-H (SEQ ID NO: 32) and mIgG2aK (SEQ ID NO: 33). The light chain constant regions can be of human kappa subtype (SEQ ID NO: 34), human lambda subtype (SEQ ID NO: 35), murine kappa subtype (SEQ ID NO: 36) or murine lambda subtype (SEQ ID NO: 37).

The prepared recombinant antibody expression plasmids were transfected into HEK293 cells (such as HEK293F, Invitrogen, Inc.) using liposomes (such as 293fectin, Invitrogen, Inc.) or other transfected reagents (such as PEI). The cells were cultured in suspension in serum-free mediums for 3-5 days. The culture supernatants were then harvested by centrifugation. The recombinant protein in the supernatant was further purified by a ProteinA/G affinity chromatography column (such as Mabselect SURE, GE, Inc.). The recombinant protein preservation buffer was then replaced with PBS (pH 7.0) or other suitable buffers by using a desalting column (such as Hitrap desalting, GE, Inc.). If necessary, the antibody sample can be sterilized by filtration and then stored in aliquots at −20° C.

Example 2: Murien Immunization and Construction of Immune Library

BALB/c mice with 6 to 8 weeks old were immunized with the recombinant protein TT-Hc-His prepared in Example 1 as the antigen at an immunization dose of 50 μg per mouse.

Boosted immunization was carried out every 14 days. The mice were sacrificed 8 weeks after prime immunization and spleen cells were harvested. Murine spleen lymphocytes were isolated by using a murine lymphocyte isolation solution (Dakewe Biotech Co., Ltd., CAT #DKW33-R0100). Total RNA was extracted from the isolated lymphocytes by using a cellular total RNA extraction kit (Tiangen Biotech (Beijing) Co., Ltd., CAT #DP430). Using the extracted total RNA as a template, the antibody heavy chain variable region and light chain variable region were synthesized using a first strand cDNA synthesis kit (Thermo scientific, CAT #K1621). The used reverse transcription primers were gene-specific primers, and the primer pairing regions were located in the heavy chain constant region and the antibody light chain constant region, respectively. The specific sequences were PmCGR: TGCATTTGAACTCCTTGCC (SEQ ID NO: 38) and PmCKR: CCATCAATCTTCCACTTGAC (SEQ ID NO: 39), respectively. The synthesized cDNA was immediately stored at −70° C. for subsequence use. Then, using the cDNA obtained by reverse transcription as a template, the primers were synthesized by referring to Krebber A, Bornhauser S, Burmester J, et al. Reliable cloning of functional antibody variable domains from hybridomas and spleen cell repertoires employing a reengineered phage display system. J Immunol Methods. 1997; 201(1):35-55, the entire contents of which are incorporated herein by reference, and the nucleotide sequences encoding the VH and VK of murine antibodies were respectively amplified by PCR. Then, the single-chain fragment variable (scFv) genes were constructed by overlapping extension PCR technology. Finally, the nucleotide sequences of the prepared murine single chain antibodies were cloned into the vector pADSCFV-S (see Example 1 in Chinese Patent Application No. 201510097117.0 for detailed experimental protocols, the entire contents of which are incorporated herein by reference) to construct a scFv library. The antibody library has a capacity of 5×10E8, and an accuracy of 50%.

Example 3: Screening and Preliminary Identification of Murine Immune Library

3.1. Screening of Murine Immune Library

Referring to Chinese Patent Application No. 201510097117.0 (the entire contents of which are incorporated herein by reference), the phage library displaying murine single chain antibodies constructed in Example 2 was screened by solid phase screening strategy (as for the experimental protocal, see, Phage Display: A Practical Approach, Tim Clackson and Henry B. Lowman (ed.), translated by Lan Ma et al., Chemical Industry Press, May 2008) using the recombinant human TT-Hc-His prepared in Example 1 as the antigen. Three rounds of screening were carried out by means of binding, elution, neutralization, infection and amplification. Finally, two single chain antibodies S22E2 and S24B8 specifically binding to human TT-Hc-His were obtained.

The nucleotide sequences encoding the heavy chain and light chains of S22E2 and S24B8 were respectively cloned into eukaryotic expression vectors carrying the nucleotide sequences encoding the mouse mIgG2a heavy chain constant region and the mouse kappa light chain constant region by using conventional molecular biological means so as to prepare the recombinant murine antibodies.

3.2. Affinity Analysis of Recombinant Anti-TT-Hc Monoclonal Antibodies

The affinities of the anti-TT-Hc antibodies were determined by the surface plasmon resonance technique using Biacore X100. Reagents and consumables such as amino-coupling kit (BR-1000-50), murine antibody capture kit (BR-1008-38), CM5 chip (BR100012) and 10×HBS-EP, pH 7.4 (BR100669) were purchased from GE healthcare. The carboxylated CM5 chip surface was activated with 1-Ethyl-3-(3-dimethylaminopropyl) carbodiimide hydrochlorid (EDC) and N-Hydroxysuccinimide (NHS) according to the instructions in the kit. An anti-mouse IgG (Fc) antibody (capture antibody) was diluted to 25 μg/mL with 10 mM sodium acetate (pH5.0), and then injected at a flow rate of 10 μL/min to achieve a coupling amount of approximately up to 10,000 response units (RU). After injection of the capture antibody, 1 M ethanolamine was injected to block unreacted groups. For the kinetics measurement, the anti-TT-Hc antibody was diluted to 0.5-1 μg/mL, and injected at 10 μL/min to ensure that approximately 50RU of the antibody was captured by the anti-murine Fc antibody. The TT-Hc-His was then set to a series of concentration gradients (e.g., 6.17 nM, 18.5 nM, 55.6 nM, 167 nM, and 500 nM) and injected at 25° C. from lower to higher concentrations at 30 μL/min, with a association time of 120 s and a dissociation time of 3,600 s. A 10 mM glycine-HCl solution (pH2.0) was injected at 10 μL/min for 30 s to regenerate the surface of the chip. The association rate (Ka) and dissociation rate (Kd) were calculated by fitting the binding and dissociation sensorgrams with a 1:1 binding model by using Biacore X100 evaluation software version 2.0.1. The dissociation equilibrium constant (KD) was calculated as the ratio $K_d/K_a$. The fitting results were shown in Table 1.

TABLE 1

| Affinity constant in binding of recombinant anti-TT-Hc monoclonal antibodies to TT-Hc-his | | | |
|---|---|---|---|
| | $K_a$ | $K_d$ | KD |
| S22E2-mIgG2a | 6.424E+4 | 1.589E−4 | 2.473E−9 |
| S24B8-mIgG2a | 5.488E+4 | 1.015E−5 | 1.849E−10 |

Example 4: Epitope Analysis of Anti-Tetanus Toxin Monoclonal Antibodies 96-well ELISA plates were coated with recombinant protein TT-Hc-His (3 μg/mL, 100 μL/well) overnight in a refrigerator at 4° C., and were then blocked with a blocking solution (PBS-0.1% Tween20-3% milk) at 37° C. for 1 hour. The S22E2-mIgG2a and S24B8-mIgG2a murine antibodies were diluted gradiently with S22E2 purified phage (S22E2 phage) of a fixed concentration (1*10¹¹ cfu/mL). The starting concentration of the antibodies was 50 μg/mL, and the dilution was carried out at 3-fold for a total of 11 concentration gradients. The antibody dilutions were added to the blocked 96-well ELISA plates at 100 μL/well and the plates were incubated at 37° C. for 1 hour. Then, the ELISA plates were washed with PBS-0.1% Tween20, followed by addition of HRP anti-M13 secondary antibody (Sino Biological Inc., 11973-MM05T-H) and the plates were incubated at 37° C. for 1 hour. The ELISA plates were washed with PBS-0.1% Tween20, and an OPD substrate developing solution was added. After incubation for 5-10 minutes, the development was terminated with 1M $H_2SO_4$. The optical density values were determined using a microplate reader at 492 nm/630 nm dual wavelength. The results from the ELISA assay (FIG. 1) showed that S22E2-mIgG2a completely inhibited the binding signal between S22E2 phage and recombinant protein TT-Hc, but S24B8-mIgG2a had no effect on binding of S22E2 phage to TT-Hc.

Figure 2:
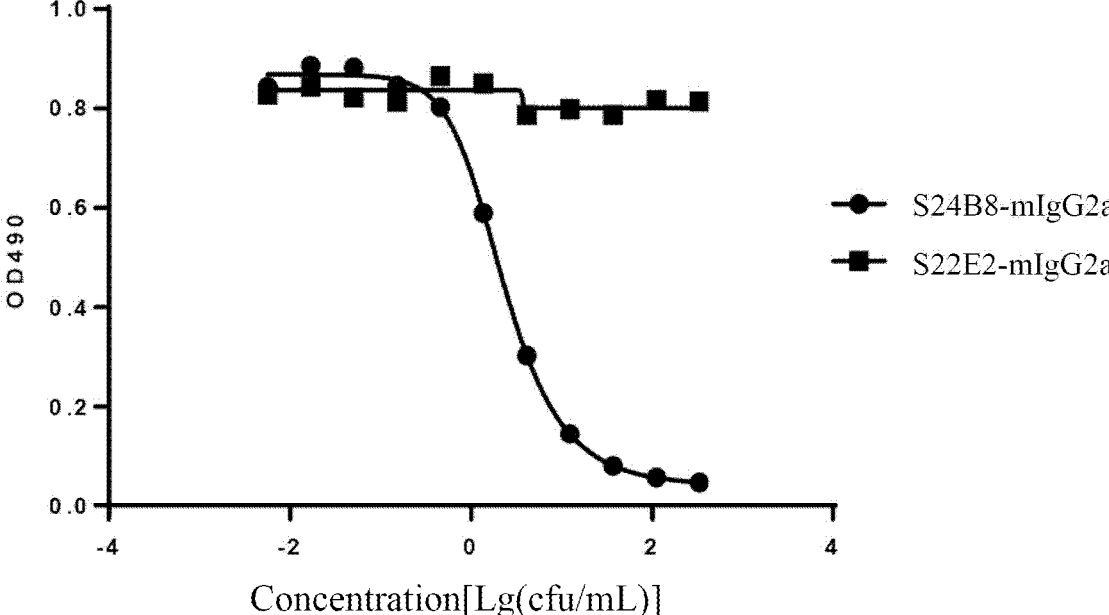
FIG. 2 shows the results from an ELISA assay assessing how anti-TT-Hc monoclonal antibodies S22E2-mIgG2a and S24B8-mIgG2a inhibit binding of S24B8 purified phage to TT-Hc.

Similarly, S22E2-mIgG2a and S24B8-mIgG2a were diluted gradiently with S24B8 purified phage (S24B8 phage) of the fixed concentration. The binding signal between S24B8 phage and TT-Hc was detected with HRP anti-M13 secondary antibody. The ELISA results (FIG. 2) showed that S24B8-mIgG2a completely inhibited the binding signal between S24B8 phage and recombinant protein TT-Hc, but S22E2-mIgG2a has little effect on binding of S24B8 phage to TT-Hc.

In summary, anti-TT-Hc monoclonal antibodies S22E2-mIgG2a and S24B8-mIgG2a bind to different epitopes of TT-Hc.

Figure 3:
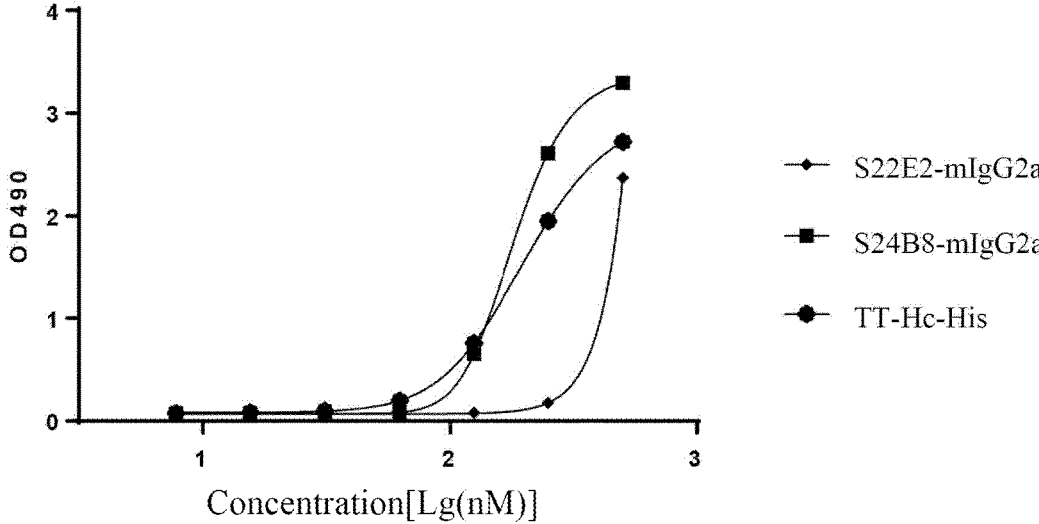
FIG. 3 shows the results from an ELISA assay assessing how anti-TT-Hc monoclonal antibodies S22E2-mIgG2a and S24B8-mIgG2a inhibit binding of TT-Hc to ganglioside GT1b.

Example 5: Inhibition of Binding of TT-Hc to Gangliosides by Anti-Tetanus Toxin Monoclonal Antibodies The tetanus toxin can bind to specific receptors on the surfaces of nerve cells via the Hc domain. Currently, the generally accepted mechanism is a dual receptor mechanism, involving a ganglioside receptor and a protein receptor. 96-well ELISA plates were coated with gangliosides GT1b (100 μL/well) which was diluted to 10 μg/mL with methanol, and the plates were left overnight at room temperature to allow the methanol to evaporate. Then, the plates were blocked with a blocking solution (PBS-0.1% Tween20-1% BSA) at 37° C. for 1 hour. TT-Hc was diluted gradiently. The starting concentration of TT-Hc was 100 μg/mL and the dilution was carried out at 3-fold for a total of 7 concentration gradients. The anti-TT-Hc murine monoclonal antibodies were diluted to 40 μg/mL with PBS and mixed with TT-Hc dilutions in equal volumes, and then the mixed solutions were added to the blocked 96-well ELISA plates at 100 μL/well. A TT-Hc control group without an antibody was set. The plates were incubated at 37° C. for 1 hour. The ELISA plates were washed with PBS-0.1% Tween20, and a HRP anti-TT polyclonal antibody (prepared in laboratory) was added at 100 μL/well. The plates were incubated at 37° C. for 1 hour. Then, the ELISA plates were washed with PBS-0.1% Tween20, and an OPD substrate developing solution was added. After incubation for 5-10 minutes, the development was terminated with 1 M $H_2SO_4$ solution, and the optical density values were determined using a microplate reader at 492 nm/630 nm dual wavelength. The results from the ELISA assay (FIG. 3) showed that, with respect to the binding curve of TT-Hc as the basis, the binding curve significantly shifted to the right after the addition of S22E2-mIgG2a, indicating that S22E2-mIgG2a effectively inhibited binding of TT-Hc to ganglioside GT1b. In contrast, S24B8-mIgG2a did not inhibit binding of TT-Hc to ganglioside, and instead showed somewhat promoting effects.

Figure 4:
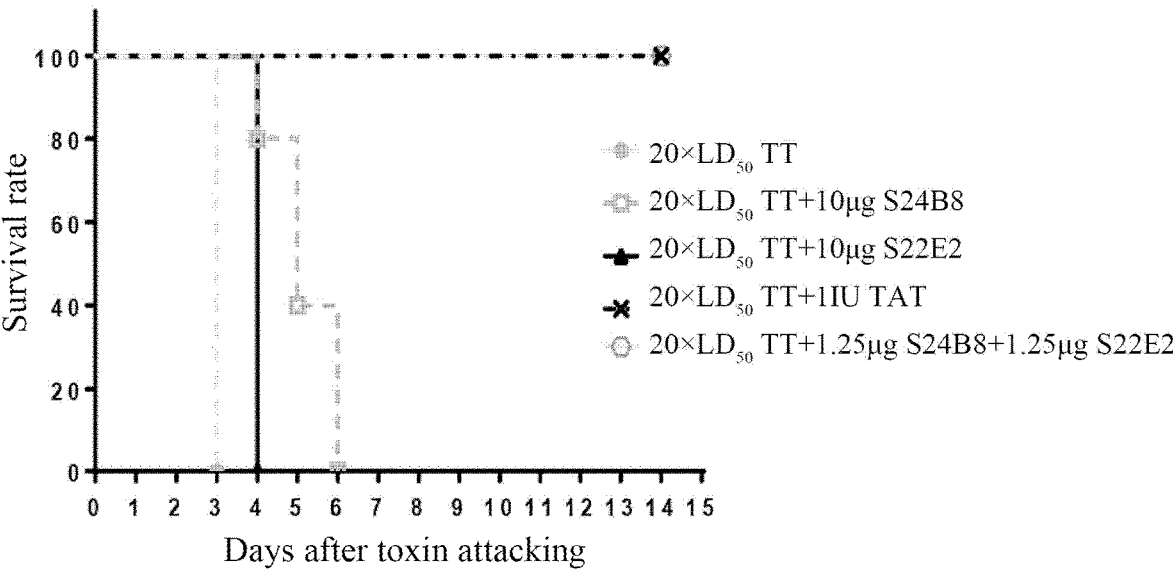
FIG. 4 shows the neutralization effects of the anti-tetanus toxin monoclonal antibodies on the tetanus toxin.

Example 6: Neutralizing Activities of Anti-Tetanus Toxin Monoclonal Antibodies The neutralizing activity of an antibody was determined by mixing the antibody and a lethal dose of tetanus toxin in vitro and then injecting the mixture into Balb/c mice. In particular, the tetanus toxin was mixed with either an anti-tetanus toxin monoclonal antibody or an antitoxin, and the mixture was left at 37° C. for 1 hour and then injected into the muscle of right hind legs of Balb/c mice. The injection dose of tetanus toxin was $20\times LD_{50}$/mouse. The injection dose of commercially available equine tetanus immuno-globulin $(F(ab')_2)$ (labeled as TAT, Shanghai Serum Bio-technology Co., LTD.) was 1 IU/mouse. The injection dose of monoclonal antibody S22E2 or S24B8 was 10 μg/mouse. The dose of S24B8 and S22E2 in combination was 1.25 μg/mouse for each antibody. Balb/c mice injected with $20\times LD_{50}$ of tetanus toxin were used as a control group. There were a total of 5 groups each of which had 8 mice. The tetanus toxin was diluted to $800\times LD_{50}$/mL with a boric acid buffer (i.e., $20\times LD_{50}$ per 50 μl of injection after mixing with the antibody in equal volumes). Equine tetanus immuno-globulin was diluted to 40 IU/mL with a boric acid buffer (i.e., 1 IU per 50 μl of injection after mixing with the tetanus toxin in equal volumes). Antibodies S22E2 and S24B8 were diluted to 0.4 mg/ml (or 0.1 mg/mL) with a boric acid buffer (i.e., for the treatment with S22E2 or S24B8, 10 μg of an antibody per 50 μl of injection after mixing with the tetanus toxin in equal volumes; and for the treatment with S24B8 and S22E2 in combination, 1.25 μg of each antibody per 50 μl of injection after mixing the two-antibody mixture (mixed in equal volumes) with the tetanus toxin in equal volumes). Each animal was injected with 50 μL of the mixture of the tetanus toxin and an antibody. The experimental results were shown in FIG. 4. All Balb/c mice in the control group died of tetanus within 3 days of the attack. Under the experimental conditions, monoclonal antibody S24B8 or S22E2 partially neutralized the toxin and prolonged the survival of the mice. In contrast, the combination of S24B8 and S22E2 completely neutralized the toxin and all mice survived by the end of the experimental period, same as the neutralizing activity observed for the equine tetanus immunoglobulin TAT.

Figure 5:
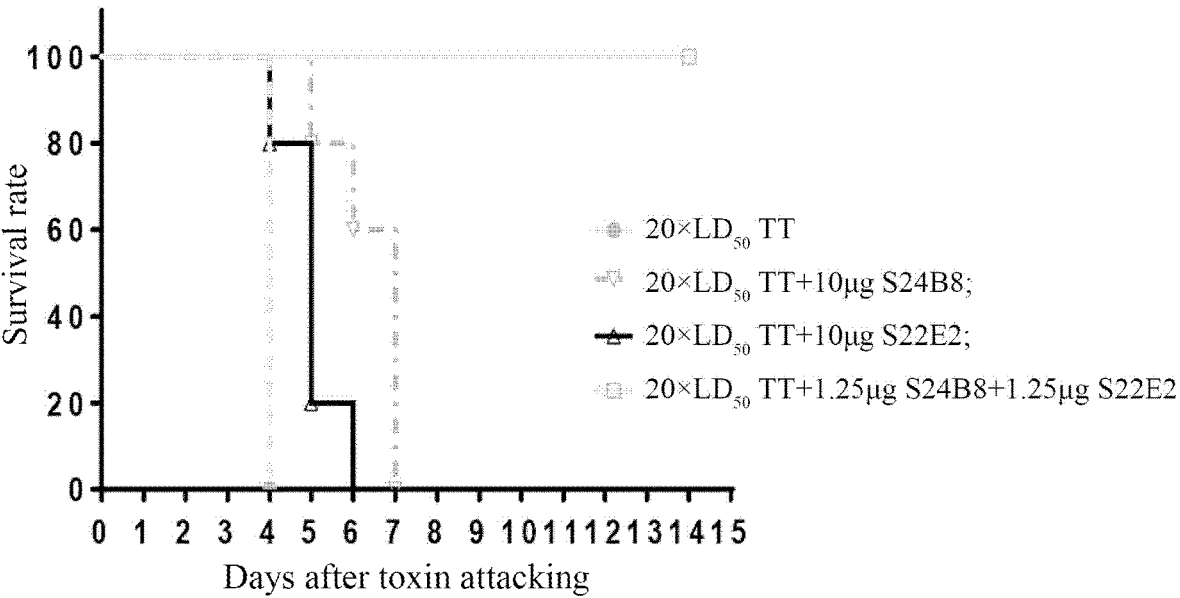
FIG. 5 shows the protective effect of the combination of anti-tetanus toxin monoclonal antibodies against lethal tetanus toxin attack in Balb/c mice.

Example 7: Protection from Combination of Anti-Tetanus Toxin Monoclonal Antibodies in Balb/c Mice Receiving Lethal Tetanus Toxin Attack Balb/c mice were subjected to immunization prior to immunoglobulin exposure and then the mice injected with an antibody were attacked with a lethal dose of tetanus toxin to determine the protective effects of the antibody. The injection dose of monoclonal antibodies S22E2 or S24B8 was 10 μg/mouse. The injection dose of S24B8 and S22E2 in combination was 1.25 μg/mouse for each antibody. Balb/c mice injected with $20\times LD_{50}$ of tetanus toxin were used as a control group. There were a total of 4 groups each of which had 8 mice. The tetanus toxin was diluted to $400\times LD_{50}$/mL with a boric acid buffer (i.e., containing $20\times LD_{50}$ per 50 μl of injection). Antibodies S22E2 and S24B8 were diluted to 0.2 mg/mL (or 0.05 mg/mL) with a boric acid buffer (i.e., for the treatment with S22E2 or S24B8, 10 μg of an antibody per 50 μl of injection; and for the treatment with S24B8 and S22E2 in combination, 1.25 μg of each antibody per 50 μl of injection after the two antibodies were mixed in equal volumes. 50 μL of anti-tetanus toxin antibodies were administered to Balb/c mice, and 24 hours later, the mice were attacked with the tetanus toxin in the muscle of right hind legs. Each animal was injcted with 50 μL of tetanus toxin. The experimental results were shown in FIG. 5. All Balb/c mice in the control group died of tetanus within 4 days of the attack. Under the experimental conditions, the combination of S24B8 and S22E2 completely protected Balb/c mice, all of which survived by the end of the experimental period.

Example 8: Humanization and Deamination Site Mutation of Anti-Tetanus Toxin Monoclonal Antibodies 8.1. Humanization of Murine Monoclonal Antibody S24B8

Murine monoclonal antibody S24B8 was humanized to reduce its immunogenicity. The humanization scheme adopted a classic framework transplantation strategy (see, Tan P, Mitchell D A, Buss T N, Holmes M A, Anasetti C, Foote J. "Superhumanized" antibodies: reduction of immunogenic potential by complementarity-determining region grafting with human germline sequences: application to an anti-CD28. J Immunol. 2002; 169(2):1119-1125, the entire contents of which are incorporated herein by reference). The genes encoding the heavy and light chain variable regions of S24B8 were compared to the human antibody germline genetic sequences in the IMGT database, respectively. Appropriate germline genetic sequences were selected to provide Framework Regions 1 to 3 of the antibody (FR1+FR2+FR3), and an appropriate J region genetic sequence was selected to provide Framework Region 4 (FR4). This template may be selected depending on a variety of factors, such as the relative total length of an antibody, the sizes of the CDRs, the amino acid residues at the junction between the framework region (FR) and the hypervariable region (CDR) of an antibody, and homology of the entire sequence. The selected template may be a mixture of multiple sequences or a common template, in order to maintain an appropriate conformation of the parental complementarity determining regions (CDR) as much as possible. Meanwhile, in order to avoid the protein heterogeneity possibly caused by the deamination site NG in the antibody hypervariable region (CDR), the heavy chain variable region of the humanized antibody was designed for mutations. Finally, three humanized heavy chain variable region mutants S24B8VH-h1(SEQ ID NO: 15), S24B8VH-h2(SEQ ID NO: 16), S24B8VH-h3(SEQ ID NO: 17) and one humanized light chain variable region mutant S24B8VK-h1(SEQ ID NO: 18) were obtained.

8.2. Humanization of Murine Monoclonal Antibody S22E2

The humanization of murine monoclonal antibody S22E2 adopted the classic framework transplantation strategy. Referring to Example 8.1, CDR grafting of the light and heavy chain variable regions of S22E2 yielded a humanized heavy chain variable region mutant S22E2VH-h1(SEQ ID NO: 19) and a humanized light chain variable region mutant S22E2VK-h1(SEQ ID NO: 20).

The variable region genes of the antibody were designed and synthesized according to the amino acid sequences of humanized antibodies of S24B8 and S22E2, and cloned into suitable eukaryotic gene expression vectors. The intact antibodies were prepared according to Example 1. Three humanized versions of S24B8 were named S24B8-h1, S24B8-h2, and S24B8-h3. The humanized version of S22E2 was named S22E2-h1.

8.3. Affinity Assay of Humanized S24B8 and S22E2

Referring to Example 3.2, the binding affinity between the humanized anti-TT-Hc antibody and TT-Hc was determined by Biacore X100 using a human antibody capture kit (BR- 1008-39). The fitting results were shown in Table 2. The heavy chain constant regions of individual humanized antibodies were all of human IgG1 subtype.

TABLE 2

| Affinity constant for binding of recombinant anti-TT-Hc monoclonal antibodies to TT-Hc-His | | |
|---|---|---|
| $K_a$ | $K_d$ | KD |
| S22E2-IgG1 | 2.042E+5 | 1.872E-4 | 9.163E-10 |
| S22E2-h1-IgG1 | 2.68E+5 | 1.535E-4 | 5.728E-10 |
| S24B8-h1-IgG1 | 7.866E+4 | <1E-5 | — |
| S24B8-h2-IgG1 | 4.447E+4 | 1.713E-5 | 3.852E-10 |
| S24B8-h3-IgG1 | 7.175E+4 | 1.178E-5 | 1.642E-10 |

Example 9: Preparation of Bispecific Antibodies

Based on the superior neutralizing activity of the combination of anti-tetanus toxin monoclonal antibodies S24B8 and S22E2 over their single treatments, antigen-binding fragments binding to different epitopes of tetanus toxin Hc protein from S24B8-h3 and S22E2-h1 were designed as a Fab and an scFv, respectively, to construct a human IgG1 heterodimer based on the KIH (Knob-Into-Hole) technology. That is, the S24B8-h3-derived antigen-binding fragment in a Fab form was fused to the N-terminus of an Fc segment containing a Knob mutation (FcK, SEQ ID NO: 40), and the S22E2-h1-derived antigen-binding fragment in a scFv form was fused to the N-terminus of an Fc segment containing a Hole mutation (FcH, SEQ ID NO: 41), thereby constructing a bispecific antibody against tetanus toxin (Hc) protein.

The three constructed eukaryotic expression vectors expressing S22E2-h1-scFv-FcH1, S24B8VH-h3+CH-IgG1K and S24B8VK-h1+CK, respectively, were co-transfected into HEK293F cells using liposomes, and the cells were cultured in suspension in a serum-free medium for 3-5 days. The culture supernatant was harvested by centrifugation. The bispecific antibodies in the culture supernatant were purified using a Protein A/G affinity chromatography column (e.g., Mabselect SURE, GE Inc.). The recombinant antibody preservation buffer was then replaced with a PBS buffer (pH 7.0) or other suitable buffers using a desalination column (e.g., Hitrap desalting, GE Inc.). The desalted protein solution was purified by a size exclusion chromatography (SEC) using Superdex 200 (GE), thereby obtaining bispecific antibody S22E2h1-scFv-FcH1+S24B8h3-IgG1K. If necessary, the antibody samples can be sterilized by filtration and then stored in aliquots at −20° C.

Figure 6:
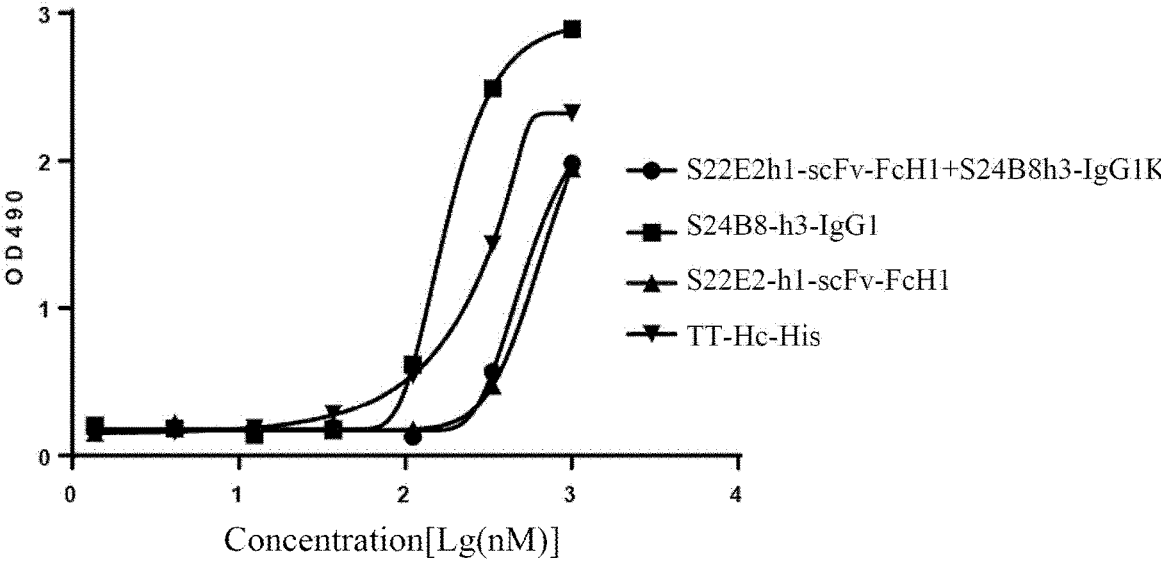
FIG. 6 shows that the bispecific antibody S22E2h1-scFv-FcH1+S24B8h3-IgG1K inhibits binding of TT-Hc to ganglioside GM1.
Figure 7:
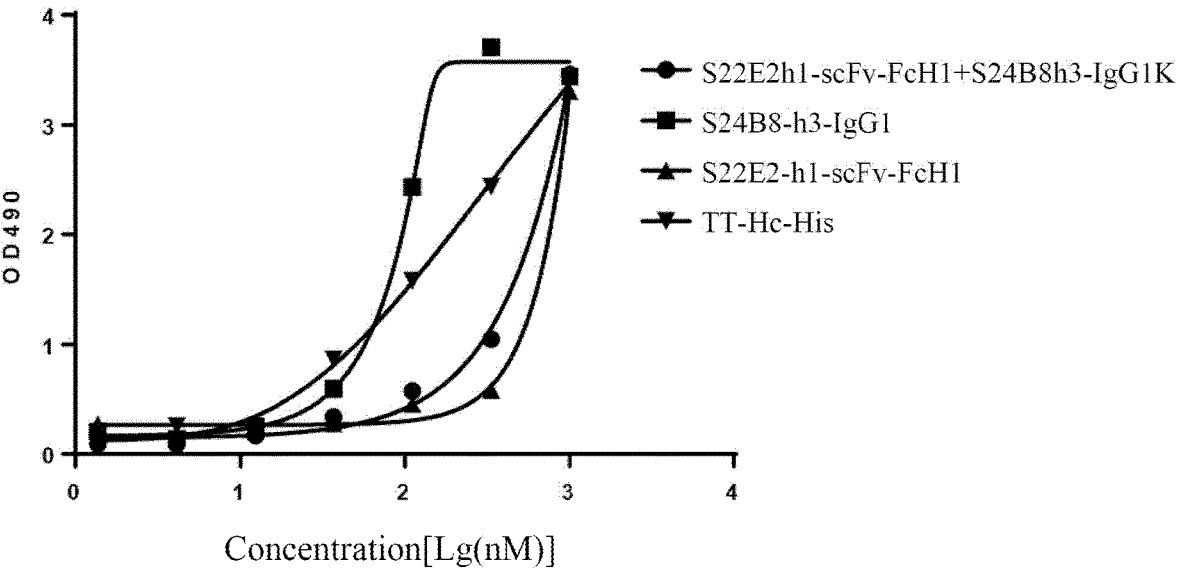
FIG. 7 shows that the bispecific antibody S22E2h1-scFv-FcH1+S24B8h3-IgG1K inhibits binding of TT-Hc to ganglioside GD3.
Figure 8:
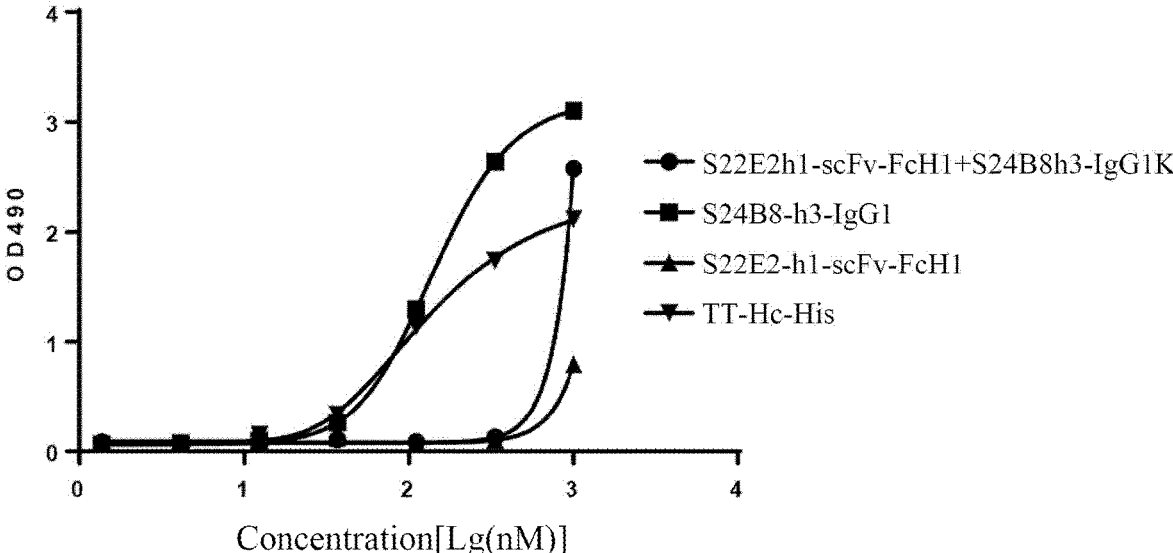
FIG. 8 shows that the bispecific antibody S22E2h1-scFv-FcH1+S24B8h3-IgG1K inhibits binding of TT-Hc to ganglioside GT1b.

Example 10: Functional Validation of Bispecific Antibodies 10.1. Inhibition of Binding of TT-Hc to Gangliosides Referring to Example 5, the inhibitory abilities of anti-TT-Hc antibodies on TT-Hc binding to three gangliosides GD3, GT1b and GM1a were determined. ELISA results (FIGS. 6, 7 and 8) showed that monoclonal antibody S22E2-h1-scFv-FcH1 and bispecific antibody S22E2h1-scFv-FcH1+S24B8h3-IgG1K had significant inhibitory effects on binding of TT-Hc to the three gangliosides, and monoclonal antibody S24B8-h3-IgG1 did not affect binding of TT-Hc to the three gangliosides.

10.2. Neutralizing Activity

Figure 9:
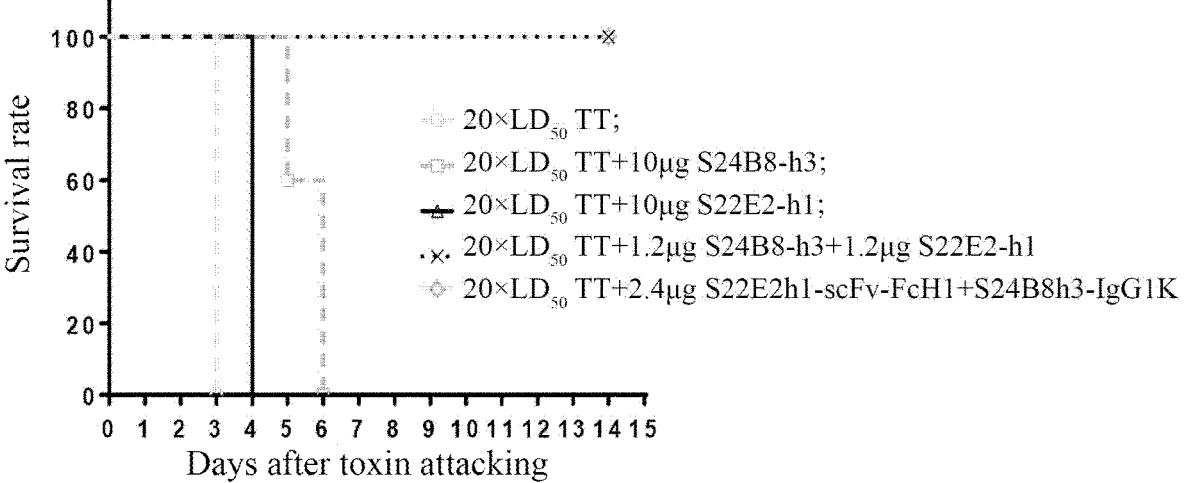
FIG. 9 shows the neutralizing activity of the anti-tetanus toxin bispecific antibody S22E2h1-scFv-FcH1+S24B8h3-IgG1K.

Referring to Example 6, the injection dose of tetanus toxin was $20 \times LD_{50}$/mouse. The injection dose of monoclonal antibody S24B8-h3 or S22E2-h1, when used alone, was 10 µg/mouse. The injection dose of monoclonal antibody S24B8-h3 and S22E2-h1 in combination was 1.2 µg/mouse for each antibody. The injection dose of bispecific antibody S22E2h1-scFv-FcH1+S24B8h3-IgG1K was 2.4 µg/mouse. Balb/c mice injected with $20 \times LD_{50}$ of tetanus toxin were used as a control group. There were a total of 5 groups with 8 mice per group. The tetanus toxin was diluted to $800 \times LD_{50}$/mL with a boric acid buffer (i.e., $20 \times LD_{50}$ per 50 µl of injection after mixing with the antibody in equal volumes). Antibodies S22E2 and S24B8 were diluted to 0.4 mg/mL (or 0.096 mg/mL) with a boric acid buffer (i.e., for the treatment with S22E2 or S24B8, 10 µg of an antibody per 50 µl of injection after mixing with the tetanus toxin in equal volumes; and for the treatment with S24B8 and S22E2 in combination, 1.2 µg of each antibody per 50 µl of injection after mixing the two-antibody mixture (mixed in equal volumes) with the tetanus toxin in equal volumes). Bispecific antibody S22E2h1-scFv-FcH1+S24B8h3-IgG1K was diluted to 0.096 mg/mL with a boric acid buffer (i.e., 2.4 µg of the bispecific antibody per 50 µl of injection after mixing with the tetanus toxin in equal volumes). Each animal was injected with 50 µL of the mixture of the tetanus toxin and an antibody. The experimental results were shown in FIG. 9. All Balb/c mice in the control group died of tetanus within 3 days of the attack, and the Balb/c mice in the combination group of S24B8-h3 and S22E2-h1 and the Balb/c mice in the group of bispecific antibody S22E2h1-scFv-FcH1+S24B8h3-IgG1K all survived by the end of the experimental period. The neutralizing activity of bispecific antibody S22E2h1-scFv-FcH1+S24B8h3-IgG1K was superior to those of the monoclonal antibodies.

Example 11: Determination of Antibody Titers

The titer of bispecific antibody S22E2h1-scFv-FcH1+S24B8h3-IgG1K was determined based on the method for determining the neutralizing activities of the antibodies in Example 6. The number of international units (IU) of anti-tetanus toxin antibody contained in 1 mg of a test sample was calculated by comparing the test sample and a standard sample. Dilution of tetanus toxin included diluting the tetanus toxin with a boric acid buffer to 40 test doses (L+1/10) per milliliter (i.e., 1 test dose (L+1/10) per 50 µl of injection after mixing with the antibody in equal volumes). Dilution of a human tetanus immunoglobulin standard included diltuting the human tetanus immunoglobulin standard with a boric acid buffer to 4 IU/mL (i.e., 1/10 IU per 50 µl of injection after mixing with the toxin in equal volumes). Bispecific antibody S22E2h1-scFv-FcH1+S24B8h3-IgG1K was diluted with a boric acid buffer to five concentrations at 15% intervals, i.e., 14.40 µg/mL, 16.80 µg/mL, 20 µg/mL, 23.6 µg/mL and 27.6 µg/mL in sequence (i.e., 0.36 µg, 0.42 µg, 0.50 µg, 0.59 µg and 0.69 µg of the bispecific antibodies per 50 µl of injection after mixing with the toxin in equal volumes). The diluted human tetanus immunoglobulin standard solutions and the solutions of the bispecific antibody at different dilutions were mixed with an equal volume of diluted tetanus toxin, respectively. Immediately after incubation for 1 hour at 37° C., the mixtures were injected to mice with an intramuscular injection volume of 50 µL per mouse. Mice were observed once a day to record incidence or death. The results showed that all Balb/c mice in the control group died of tetanus within 72 hours after the attack, and the highest dose of the bispecific antibody in the group, in which the mice died simultaneously with the mice in the control group, was 0.42 µg, the titer of which was calculated to be 238 IU/mg.

While the present inventions have been described in detail with reference to the general description and specific examples, it will be apparent to those skilled in the art that some modifications and improvements may be made to the present inventions. Accordingly, such modifications and improvements made without departing from the spirit of the inventions fall within the scopes of the inventions as claimed.

REFERENCE

1. Thwaites C L, Beeching N J, Newton C R (2015) Maternal and neonatal tetanus. Lancet 385:362-370.
2. Yousefi M, Tahmasebi F, Younesi V, Razavi A, Khoshnoodi J, Bayat A A, Abbasi E, Rabbani H, Jeddi-tehrani M, Shokri F (2014a) Characterization of neutralizing monoclonal antibodies directed against tetanus toxin fragment C. J Immunotoxicol 11:28-34.
3. Ashton A C, Li Y, Doussau F, Weller U, Dougan G, Poulain B, Dolly J O (1995) tetanus toxin inhibits neuroexocytosis even when its Zn21-dependent protease activity is removed.
4. Scott N, Qazi O, Wright M J, Fairweather N F, Deonarain M P (2010) Characterisation of a panel of anti-tetanus toxin single-chain Fvs reveals cooperative binding. Mol Immunol 47:1931-1941.
5. Yousefi M, Khosravi-Eghbal R, Reza Mahmoudi A, Jeddi-Tehrani M, Rabbani H, Shokri F (2014b) Comparative in vitro and in vivo assessment of toxin neutralization by anti-tetanus toxin monoclonal antibodies. Hum Vaccin Immunother 10:344-351.
6. Petrusic V, Zivkovic I, Stojanovic M, Stojicevic I, Marinkovic E,Dimitrijevic L (2012) Production, characterization and applications of a tetanus toxin specific monoclonal antibody T-62. Acta Histochem 114:480-486.
7. Lang A B, Cryz S J Jr, Schurch U, Ganss M T, Bruderer U (1993) Immunotherapy with human monoclonal antibodies. Fragment A specificity of polyclonal and monoclonal antibodies is crucial for full protection against tetanus toxin. J Immunol 151:466-472.

What is claimed is:

1. A bispecific antibody comprising a first antigen-binding fragment and a second antigen-binding fragment that bind to different epitopes of a tetanus toxin, wherein the bispecific antibody has activity of neutralizing the tetanus toxin, wherein the first antigen-binding fragment comprises:

heavy chain complementarity determining region 1 (HCDR1) having the amino acid sequence of SYWIY (SEQ ID NO: 1), heavy chain complementarity determining region 2 (HCDR2) having the amino acid sequence of EINPTNGFANYNEKFKT (SEQ ID NO: 2) or EINPTAGFANYNEKFKT (SEQ ID NO: 3) or EINPTNAFANYNEKFKT (SEQ ID NO: 4), heavy chain complementarity determining region 3 (HCDR3) having the amino acid sequence of HFRFPY (SEQ ID NO: 5), light chain complementarity determining region 1 (LCDR1) having the amino acid sequence of RASQ-DIGSSLT (SEQ ID NO: 6), light chain complementarity determining region 2 (LCDR2) having the amino acid sequence of ATSSLDS (SEQ ID NO: 7), and light chain complementarity determining region 3 (LCDR3) having the amino acid sequence of LQYASSPYT (SEQ ID NO: 8); and wherein the second antigen-binding fragment comprises:

HCDR1 having the amino acid sequence of DYGVN (SEQ ID NO: 9),

HCDR2 having the amino acid sequence of MIWSDGTTDYSSALKS (SEQ ID NO: 10),

HCDR3 having the amino acid sequence of VDGYSHYYAMDY (SEQ ID NO: 11),

LCDR1 having the amino acid sequence of RASENIY-SYLA (SEQ ID NO: 12),

LCDR2 having the amino acid sequence of NAKTLAE (SEQ ID NO: 13), and

LCDR3 having the amino acid sequence of QHHYGLPFT (SEQ ID NO: 14);

wherein the HCDR and LCDR amino acid sequences are defined according to Kabat.

2. The bispecific antibody of claim 1, wherein the amino acid sequence of the heavy chain variable region of the first antigen-binding fragment is as set forth in SEQ ID NO: 15, and the amino acid sequence of the light chain variable region of the first antigen-binding fragment is as set forth in SEQ ID NO: 18; or the amino acid sequence of the heavy chain variable region of the first antigen-binding fragment is set forth in SEQ ID NO: 16, and the amino acid sequence of the light chain variable region of the first antigen-binding fragment is as set forth in SEQ ID NO: 18; or the amino acid sequence of the heavy chain variable region of the first antigen-binding fragment is as set forth in SEQ ID NO: 17, and the amino acid sequence of the light chain variable region of the first antigen-binding fragment is as set forth in SEQ ID NO: 18.

3. The bispecific antibody of claim 1, wherein the amino acid sequence of the heavy chain variable region of the second antigen-binding fragment is as set forth in SEQ ID NO: 19, and the amino acid sequence of the light chain variable region of the second antigen-binding fragment is as set forth in SEQ ID NO: 20.

4. The bispecific antibody of claim 1, wherein the forms of the first antigen-binding fragment and the second antigen-binding fragment are independently selected from a single-chain fragment variable (scFv) or a Fab fragment.

5. A monoclonal antibody that binds to a tetanus toxin, comprising:

HCDR1 having the amino acid sequence of SYWIY (SEQ ID NO: 1),

HCDR2 having the amino acid sequence of EINPTNGFANYNEKFKT (SEQ ID NO: 2) or EINPTAGFANYNEKFKT (SEQ ID NO: 3) or EINPT-NAFANYNEKFKT (SEQ ID NO: 4), HCDR3 having the amino acid sequence of HFRFPY (SEQ ID NO: 5), LCDR1 having the amino acid sequence of RASQ-DIGSSLT (SEQ ID NO: 6), LCDR2 having the amino acid sequence of ATSSLDS (SEQ ID NO: 7), and LCDR3 having the amino acid sequence of LQYASSPYT (SEQ ID NO: 8);

wherein the HCDR and LCDR amino acid sequences are defined according to Kabat.

6. A monoclonal antibody that binds to a tetanus toxin, comprising:

HCDR1 having the amino acid sequence of DYGVN (SEQ ID NO: 9),

HCDR2 having the amino acid sequence of MIWSDGTTDYSSALKS (SEQ ID NO: 10), HCDR3 having the amino acid sequence of VDGYSHY-YAMDY (SEQ ID NO: 11), LCDR1 having the amino acid sequence of RASENIYSYLA (SEQ ID NO: 12), LCDR2 having the amino acid sequence of NAKTLAE (SEQ ID NO: 13), and LCDR3 having the amino acid sequence of QHHYGLPFT (SEQ ID NO: 14);

wherein the HCDR and LCDR amino acid sequences are defined according to Kabat.

7. A pharmaceutical composition comprising the bispecific antibody of claim 1, and a pharmaceutically acceptable excipient, diluent or carrier.

8. A method of preventing or treating tetanus comprising administering to a subject in need thereof the bispecific antibody of claim 1.

9. The bispecific antibody of claim 1, wherein the first antigen-binding fragment is a Fab fragment, and the second antigen-binding fragment is a single-chain fragment variable (scFv).

10. The bispecific antibody of claim 1, wherein the bispecific antibody comprises the amino acid sequence set forth in one of SEQ ID NOs: 21, 22 and 23 and the amino acid sequence set forth in SEQ ID NO: 24.

11. The bispecific antibody of claim 1, wherein the bispecific antibody comprises the amino acid sequence set forth in SEQ ID NO: 25.

12. The monoclonal antibody of claim 5, wherein the monoclonal antibody comprises:

a heavy chain variable region amino acid sequence set forth in SEQ ID NO: 15, and a light chain variable region amino acid sequence set forth in SEQ ID NO: 18; or a heavy chain variable region amino acid sequence set forth in SEQ ID NO: 16, and a light chain variable region amino acid sequence set forth in SEQ ID NO: 18; or a heavy chain variable region amino acid sequence set forth in SEQ ID NO: 17, and a light chain variable region amino acid sequence set forth in SEQ ID NO: 18.

13. The monoclonal antibody of claim 6, wherein the monoclonal antibody comprises a heavy chain variable region amino acid sequence set forth in SEQ ID NO: 19, and a light chain variable region amino acid sequence set forth in SEQ ID NO: 20.

\* \* \* \* \*

SEQUENCE LISTING

<160> NUMBER OF SEQ ID NOS: 41

<210> SEQ ID NO 1
<211> LENGTH: 5
<212> TYPE: PRT
<213> ORGANISM: Artificial Sequence
<220> FEATURE:

<223> OTHER INFORMATION: Synthetic Polypeptide

<400> SEQUENCE: 1

Ser Tyr Trp Ile Tyr
1               5

<210> SEQ ID NO 2
<211> LENGTH: 17
<212> TYPE: PRT
<213> ORGANISM: Artificial Sequence
<220> FEATURE:
<223> OTHER INFORMATION: Synthetic Polypeptide

<400> SEQUENCE: 2

Glu Ile Asn Pro Thr Asn Gly Phe Ala Asn Tyr Asn Glu Lys Phe Lys
1               5                   10                  15

Thr

<210> SEQ ID NO 3
<211> LENGTH: 17
<212> TYPE: PRT
<213> ORGANISM: Artificial Sequence
<220> FEATURE:
<223> OTHER INFORMATION: Synthetic Polypeptide

<400> SEQUENCE: 3

Glu Ile Asn Pro Thr Ala Gly Phe Ala Asn Tyr Asn Glu Lys Phe Lys
1               5                   10                  15

Thr

<210> SEQ ID NO 4
<211> LENGTH: 17
<212> TYPE: PRT
<213> ORGANISM: Artificial Sequence
<220> FEATURE:
<223> OTHER INFORMATION: Synthetic Polypeptide

<400> SEQUENCE: 4

Glu Ile Asn Pro Thr Asn Ala Phe Ala Asn Tyr Asn Glu Lys Phe Lys
1               5                   10                  15

Thr

<210> SEQ ID NO 5
<211> LENGTH: 6
<212> TYPE: PRT
<213> ORGANISM: Artificial Sequence
<220> FEATURE:
<223> OTHER INFORMATION: Synthetic Polypeptide

<400> SEQUENCE: 5

His Phe Arg Phe Pro Tyr
1               5

<210> SEQ ID NO 6
<211> LENGTH: 11
<212> TYPE: PRT
<213> ORGANISM: Artificial Sequence
<220> FEATURE:
<223> OTHER INFORMATION: Synthetic Polypeptide

<400> SEQUENCE: 6

Arg Ala Ser Gln Asp Ile Gly Ser Ser Leu Thr
1               5                   10

-continued

```
<210> SEQ ID NO 7
<211> LENGTH: 7
<212> TYPE: PRT
<213> ORGANISM: Artificial Sequence
<220> FEATURE:
<223> OTHER INFORMATION: Synthetic Polypeptide

<400> SEQUENCE: 7

Ala Thr Ser Ser Leu Asp Ser
1               5

<210> SEQ ID NO 8
<211> LENGTH: 9
<212> TYPE: PRT
<213> ORGANISM: Artificial Sequence
<220> FEATURE:
<223> OTHER INFORMATION: Synthetic Polypeptide

<400> SEQUENCE: 8

Leu Gln Tyr Ala Ser Ser Pro Tyr Thr
1               5

<210> SEQ ID NO 9
<211> LENGTH: 5
<212> TYPE: PRT
<213> ORGANISM: Artificial Sequence
<220> FEATURE:
<223> OTHER INFORMATION: Synthetic Polypeptide

<400> SEQUENCE: 9

Asp Tyr Gly Val Asn
1               5

<210> SEQ ID NO 10
<211> LENGTH: 16
<212> TYPE: PRT
<213> ORGANISM: Artificial Sequence
<220> FEATURE:
<223> OTHER INFORMATION: Synthetic Polypeptide

<400> SEQUENCE: 10

Met Ile Trp Ser Asp Gly Thr Thr Asp Tyr Ser Ser Ala Leu Lys Ser
1               5                   10                  15

<210> SEQ ID NO 11
<211> LENGTH: 12
<212> TYPE: PRT
<213> ORGANISM: Artificial Sequence
<220> FEATURE:
<223> OTHER INFORMATION: Synthetic Polypeptide

<400> SEQUENCE: 11

Val Asp Gly Tyr Ser His Tyr Tyr Ala Met Asp Tyr
1               5                   10

<210> SEQ ID NO 12
<211> LENGTH: 11
<212> TYPE: PRT
<213> ORGANISM: Artificial Sequence
<220> FEATURE:
<223> OTHER INFORMATION: Synthetic Polypeptide

<400> SEQUENCE: 12

Arg Ala Ser Glu Asn Ile Tyr Ser Tyr Leu Ala
1               5                   10

<210> SEQ ID NO 13
```

```
<211> LENGTH: 7
<212> TYPE: PRT
<213> ORGANISM: Artificial Sequence
<220> FEATURE:
<223> OTHER INFORMATION: Synthetic Polypeptide

<400> SEQUENCE: 13

Asn Ala Lys Thr Leu Ala Glu
1               5

<210> SEQ ID NO 14
<211> LENGTH: 9
<212> TYPE: PRT
<213> ORGANISM: Artificial Sequence
<220> FEATURE:
<223> OTHER INFORMATION: Synthetic Polypeptide

<400> SEQUENCE: 14

Gln His His Tyr Gly Leu Pro Phe Thr
1               5

<210> SEQ ID NO 15
<211> LENGTH: 115
<212> TYPE: PRT
<213> ORGANISM: Artificial Sequence
<220> FEATURE:
<223> OTHER INFORMATION: Synthetic Polypeptide

<400> SEQUENCE: 15

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Thr Phe Thr Ser Tyr
            20                  25                  30

Trp Ile Tyr Trp Val Arg Gln Ala Pro Gly Gln Gly Leu Glu Trp Ile
        35                  40                  45

Gly Glu Ile Asn Pro Thr Asn Gly Phe Ala Asn Tyr Asn Glu Lys Phe
    50                  55                  60

Lys Thr Lys Ala Thr Ile Thr Val Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Ile His Phe Arg Phe Pro Tyr Trp Gly Gln Gly Thr Met Val Thr
            100                 105                 110

Val Ser Ser
        115

<210> SEQ ID NO 16
<211> LENGTH: 115
<212> TYPE: PRT
<213> ORGANISM: Artificial Sequence
<220> FEATURE:
<223> OTHER INFORMATION: Synthetic Polypeptide

<400> SEQUENCE: 16

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Thr Phe Thr Ser Tyr
            20                  25                  30

Trp Ile Tyr Trp Val Arg Gln Ala Pro Gly Gln Gly Leu Glu Trp Ile
        35                  40                  45

Gly Glu Ile Asn Pro Thr Ala Gly Phe Ala Asn Tyr Asn Glu Lys Phe
    50                  55                  60
```

```
Lys Thr Lys Ala Thr Ile Thr Val Asp Lys Ser Thr Ser Thr Ala Tyr
65              70              75              80

Met Glu Leu Ser Ser Leu Arg Ser Glu Asp Thr Ala Val Tyr Tyr Cys
            85              90              95

Ala Ile His Phe Arg Phe Pro Tyr Trp Gly Gln Gly Thr Met Val Thr
            100             105             110

Val Ser Ser
        115
```

<210> SEQ ID NO 17
<211> LENGTH: 115
<212> TYPE: PRT
<213> ORGANISM: Artificial Sequence
<220> FEATURE:
<223> OTHER INFORMATION: Synthetic Polypeptide

<400> SEQUENCE: 17

```
Gln Val Gln Leu Val Gln Ser Gly Ala Glu Val Lys Lys Pro Gly Ser
1               5               10              15

Ser Val Lys Val Ser Cys Lys Ala Ser Gly Tyr Thr Phe Thr Ser Tyr
            20              25              30

Trp Ile Tyr Trp Val Arg Gln Ala Pro Gly Gln Gly Leu Glu Trp Ile
        35              40              45

Gly Glu Ile Asn Pro Thr Asn Ala Phe Ala Asn Tyr Asn Glu Lys Phe
        50              55              60

Lys Thr Lys Ala Thr Ile Thr Val Asp Lys Ser Thr Ser Thr Ala Tyr
65              70              75              80

Met Glu Leu Ser Ser Leu Arg Ser Glu Asp Thr Ala Val Tyr Tyr Cys
            85              90              95

Ala Ile His Phe Arg Phe Pro Tyr Trp Gly Gln Gly Thr Met Val Thr
            100             105             110

Val Ser Ser
        115
```

<210> SEQ ID NO 18
<211> LENGTH: 107
<212> TYPE: PRT
<213> ORGANISM: Artificial Sequence
<220> FEATURE:
<223> OTHER INFORMATION: Synthetic Polypeptide

<400> SEQUENCE: 18

```
Asp Ile Gln Met Thr Gln Ser Pro Ser Ser Leu Ser Ala Ser Val Gly
1               5               10              15

Asp Arg Val Thr Ile Thr Cys Arg Ala Ser Gln Asp Ile Gly Ser Ser
            20              25              30

Leu Thr Trp Leu Gln Gln Lys Pro Gly Lys Ala Pro Lys Arg Leu Ile
        35              40              45

Tyr Ala Thr Ser Ser Leu Asp Ser Gly Val Pro Ser Arg Phe Ser Gly
        50              55              60

Ser Gly Ser Gly Thr Asp Tyr Thr Leu Thr Ile Ser Ser Leu Gln Pro
65              70              75              80

Glu Asp Phe Ala Thr Tyr Tyr Cys Leu Gln Tyr Ala Ser Ser Pro Tyr
            85              90              95

Thr Phe Gly Gln Gly Thr Lys Leu Glu Ile Lys
        100             105
```

-continued

```
<210> SEQ ID NO 19
<211> LENGTH: 120
<212> TYPE: PRT
<213> ORGANISM: Artificial Sequence
<220> FEATURE:
<223> OTHER INFORMATION: Synthetic Polypeptide

<400> SEQUENCE: 19

Gln Val Thr Leu Lys Glu Ser Gly Pro Val Leu Val Lys Pro Thr Glu
1               5                   10                  15

Thr Leu Thr Leu Thr Cys Thr Val Ser Gly Phe Ser Leu Thr Asp Tyr
            20                  25                  30

Gly Val Asn Trp Ile Arg Gln Pro Pro Gly Lys Ala Leu Glu Trp Leu
        35                  40                  45

Gly Met Ile Trp Ser Asp Gly Thr Thr Asp Tyr Ser Ser Ala Leu Lys
    50                  55                  60

Ser Arg Leu Thr Ile Ser Lys Asp Thr Ser Lys Ser Gln Val Val Leu
65                  70                  75                  80

Thr Met Thr Asn Met Asp Pro Val Asp Thr Ala Thr Tyr Tyr Cys Ala
                85                  90                  95

Arg Val Asp Gly Tyr Ser His Tyr Tyr Ala Met Asp Tyr Trp Gly Gln
            100                 105                 110

Gly Thr Leu Val Thr Val Ser Ser
        115                 120

<210> SEQ ID NO 20
<211> LENGTH: 107
<212> TYPE: PRT
<213> ORGANISM: Artificial Sequence
<220> FEATURE:
<223> OTHER INFORMATION: Synthetic Polypeptide

<400> SEQUENCE: 20

Asp Ile Gln Met Thr Gln Ser Pro Ser Ser Leu Ser Ala Ser Val Gly
1               5                   10                  15

Asp Arg Val Thr Ile Thr Cys Arg Ala Ser Glu Asn Ile Tyr Ser Tyr
            20                  25                  30

Leu Ala Trp Tyr Gln Gln Lys Gln Gly Lys Ala Pro Gln Leu Leu Ile
        35                  40                  45

Tyr Asn Ala Lys Thr Leu Ala Glu Gly Val Ser Ser Arg Phe Ser Gly
    50                  55                  60

Ser Gly Ser Gly Thr Gln Phe Thr Leu Thr Ile Ser Ser Leu Gln Pro
65                  70                  75                  80

Glu Asp Phe Ala Thr Tyr Tyr Cys Gln His His Tyr Gly Leu Pro Phe
                85                  90                  95

Thr Phe Gly Gln Gly Thr Lys Leu Glu Ile Lys
            100                 105

<210> SEQ ID NO 21
<211> LENGTH: 445
<212> TYPE: PRT
<213> ORGANISM: Artificial Sequence
<220> FEATURE:
<223> OTHER INFORMATION: Synthetic Polypeptide

<400> SEQUENCE: 21

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Thr Phe Thr Ser Tyr
            20                  25                  30
```

-continued

```
Trp Ile Tyr Trp Val Arg Gln Ala Pro Gly Gln Gly Leu Glu Trp Ile
        35                  40                  45

Gly Glu Ile Asn Pro Thr Asn Gly Phe Ala Asn Tyr Asn Glu Lys Phe
    50                  55                  60

Lys Thr Lys Ala Thr Ile Thr Val Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Ile His Phe Arg Phe Pro Tyr Trp Gly Gln Gly Thr Met Val Thr
                100                 105                 110

Val Ser Ser Ala Ser Thr Lys Gly Pro Ser Val Phe Pro Leu Ala Pro
            115                 120                 125

Ser Ser Lys Ser Thr Ser Gly Gly Thr Ala Ala Leu Gly Cys Leu Val
        130                 135                 140

Lys Asp Tyr Phe Pro Glu Pro Val Thr Val Ser Trp Asn Ser Gly Ala
145                 150                 155                 160

Leu Thr Ser Gly Val His Thr Phe Pro Ala Val Leu Gln Ser Ser Gly
                165                 170                 175

Leu Tyr Ser Leu Ser Ser Val Val Thr Val Pro Ser Ser Ser Leu Gly
            180                 185                 190

Thr Gln Thr Tyr Ile Cys Asn Val Asn His Lys Pro Ser Asn Thr Lys
        195                 200                 205

Val Asp Lys Arg Val Glu Pro Lys Ser Cys Asp Lys Thr His Thr Cys
    210                 215                 220

Pro Pro Cys Pro Ala Pro Glu Leu Leu Gly Gly Pro Ser Val Phe Leu
225                 230                 235                 240

Phe Pro Pro Lys Pro Lys Asp Thr Leu Met Ile Ser Arg Thr Pro Glu
                245                 250                 255

Val Thr Cys Val Val Val Asp Val Ser His Glu Asp Pro Glu Val Lys
            260                 265                 270

Phe Asn Trp Tyr Val Asp Gly Val Glu Val His Asn Ala Lys Thr Lys
        275                 280                 285

Pro Arg Glu Glu Gln Tyr Asn Ser Thr Tyr Arg Val Val Ser Val Leu
    290                 295                 300

Thr Val Leu His Gln Asp Trp Leu Asn Gly Lys Glu Tyr Lys Cys Lys
305                 310                 315                 320

Val Ser Asn Lys Ala Leu Pro Ala Pro Ile Glu Lys Thr Ile Ser Lys
                325                 330                 335

Ala Lys Gly Gln Pro Arg Glu Pro Gln Val Tyr Thr Leu Pro Pro Cys
                340                 345                 350

Arg Glu Glu Met Thr Lys Asn Gln Val Ser Leu Trp Cys Leu Val Lys
            355                 360                 365

Gly Phe Tyr Pro Ser Asp Ile Ala Val Glu Trp Glu Ser Asn Gly Gln
    370                 375                 380

Pro Glu Asn Asn Tyr Lys Thr Thr Pro Pro Val Leu Asp Ser Asp Gly
385                 390                 395                 400

Ser Phe Phe Leu Tyr Ser Lys Leu Thr Val Asp Lys Ser Arg Trp Gln
                405                 410                 415

Gln Gly Asn Val Phe Ser Cys Ser Val Met His Glu Ala Leu His Asn
                420                 425                 430

His Tyr Thr Gln Lys Ser Leu Ser Leu Ser Pro Gly Lys
            435                 440                 445
```

-continued

<210> SEQ ID NO 22
<211> LENGTH: 445
<212> TYPE: PRT
<213> ORGANISM: Artificial Sequence
<220> FEATURE:
<223> OTHER INFORMATION: Synthetic Polypeptide

<400> SEQUENCE: 22

```
Gln Val Gln Leu Val Gln Ser Gly Ala Glu Val Lys Lys Pro Gly Ser
1               5                   10                  15

Ser Val Lys Val Ser Cys Lys Ala Ser Gly Tyr Thr Phe Thr Ser Tyr
                20                  25                  30

Trp Ile Tyr Trp Val Arg Gln Ala Pro Gly Gln Gly Leu Glu Trp Ile
            35                  40                  45

Gly Glu Ile Asn Pro Thr Ala Gly Phe Ala Asn Tyr Asn Glu Lys Phe
        50                  55                  60

Lys Thr Lys Ala Thr Ile Thr Val Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Ile His Phe Arg Phe Pro Tyr Trp Gly Gln Gly Thr Met Val Thr
            100                 105                 110

Val Ser Ser Ala Ser Thr Lys Gly Pro Ser Val Phe Pro Leu Ala Pro
        115                 120                 125

Ser Ser Lys Ser Thr Ser Gly Gly Thr Ala Ala Leu Gly Cys Leu Val
    130                 135                 140

Lys Asp Tyr Phe Pro Glu Pro Val Thr Val Ser Trp Asn Ser Gly Ala
145                 150                 155                 160

Leu Thr Ser Gly Val His Thr Phe Pro Ala Val Leu Gln Ser Ser Gly
                165                 170                 175

Leu Tyr Ser Leu Ser Ser Val Val Thr Val Pro Ser Ser Ser Leu Gly
            180                 185                 190

Thr Gln Thr Tyr Ile Cys Asn Val Asn His Lys Pro Ser Asn Thr Lys
        195                 200                 205

Val Asp Lys Arg Val Glu Pro Lys Ser Cys Asp Lys Thr His Thr Cys
    210                 215                 220

Pro Pro Cys Pro Ala Pro Glu Leu Leu Gly Gly Pro Ser Val Phe Leu
225                 230                 235                 240

Phe Pro Pro Lys Pro Lys Asp Thr Leu Met Ile Ser Arg Thr Pro Glu
                245                 250                 255

Val Thr Cys Val Val Val Asp Val Ser His Glu Asp Pro Glu Val Lys
            260                 265                 270

Phe Asn Trp Tyr Val Asp Gly Val Glu Val His Asn Ala Lys Thr Lys
        275                 280                 285

Pro Arg Glu Glu Gln Tyr Asn Ser Thr Tyr Arg Val Val Ser Val Leu
    290                 295                 300

Thr Val Leu His Gln Asp Trp Leu Asn Gly Lys Glu Tyr Lys Cys Lys
305                 310                 315                 320

Val Ser Asn Lys Ala Leu Pro Ala Pro Ile Glu Lys Thr Ile Ser Lys
                325                 330                 335

Ala Lys Gly Gln Pro Arg Glu Pro Gln Val Tyr Thr Leu Pro Pro Cys
            340                 345                 350

Arg Glu Glu Met Thr Lys Asn Gln Val Ser Leu Trp Cys Leu Val Lys
        355                 360                 365
```

-continued

```
Gly Phe Tyr Pro Ser Asp Ile Ala Val Glu Trp Glu Ser Asn Gly Gln
    370             375             380

Pro Glu Asn Asn Tyr Lys Thr Thr Pro Pro Val Leu Asp Ser Asp Gly
385             390             395             400

Ser Phe Phe Leu Tyr Ser Lys Leu Thr Val Asp Lys Ser Arg Trp Gln
            405             410             415

Gln Gly Asn Val Phe Ser Cys Ser Val Met His Glu Ala Leu His Asn
            420             425             430

His Tyr Thr Gln Lys Ser Leu Ser Leu Ser Pro Gly Lys
        435             440             445

<210> SEQ ID NO 23
<211> LENGTH: 445
<212> TYPE: PRT
<213> ORGANISM: Artificial Sequence
<220> FEATURE:
<223> OTHER INFORMATION: Synthetic Polypeptide

<400> SEQUENCE: 23

Gln Val Gln Leu Val Gln Ser Gly Ala Glu Val Lys Lys Pro Gly Ser
1               5               10              15

Ser Val Lys Val Ser Cys Lys Ala Ser Gly Tyr Thr Phe Thr Ser Tyr
            20              25              30

Trp Ile Tyr Trp Val Arg Gln Ala Pro Gly Gln Gly Leu Glu Trp Ile
        35              40              45

Gly Glu Ile Asn Pro Thr Asn Ala Phe Ala Asn Tyr Asn Glu Lys Phe
    50              55              60

Lys Thr Lys Ala Thr Ile Thr Val Asp Lys Ser Thr Ser Thr Ala Tyr
65              70              75              80

Met Glu Leu Ser Ser Leu Arg Ser Glu Asp Thr Ala Val Tyr Tyr Cys
            85              90              95

Ala Ile His Phe Arg Phe Pro Tyr Trp Gly Gln Gly Thr Met Val Thr
            100             105             110

Val Ser Ser Ala Ser Thr Lys Gly Pro Ser Val Phe Pro Leu Ala Pro
        115             120             125

Ser Ser Lys Ser Thr Ser Gly Gly Thr Ala Ala Leu Gly Cys Leu Val
    130             135             140

Lys Asp Tyr Phe Pro Glu Pro Val Thr Val Ser Trp Asn Ser Gly Ala
145             150             155             160

Leu Thr Ser Gly Val His Thr Phe Pro Ala Val Leu Gln Ser Ser Gly
            165             170             175

Leu Tyr Ser Leu Ser Ser Val Val Thr Val Pro Ser Ser Ser Leu Gly
            180             185             190

Thr Gln Thr Tyr Ile Cys Asn Val Asn His Lys Pro Ser Asn Thr Lys
        195             200             205

Val Asp Lys Arg Val Glu Pro Lys Ser Cys Asp Lys Thr His Thr Cys
    210             215             220

Pro Pro Cys Pro Ala Pro Glu Leu Leu Gly Gly Pro Ser Val Phe Leu
225             230             235             240

Phe Pro Pro Lys Pro Lys Asp Thr Leu Met Ile Ser Arg Thr Pro Glu
            245             250             255

Val Thr Cys Val Val Val Asp Val Ser His Glu Asp Pro Glu Val Lys
            260             265             270

Phe Asn Trp Tyr Val Asp Gly Val Glu Val His Asn Ala Lys Thr Lys
        275             280             285
```

-continued

```
Pro Arg Glu Glu Gln Tyr Asn Ser Thr Tyr Arg Val Val Ser Val Leu
    290                 295                 300

Thr Val Leu His Gln Asp Trp Leu Asn Gly Lys Glu Tyr Lys Cys Lys
305                 310                 315                 320

Val Ser Asn Lys Ala Leu Pro Ala Pro Ile Glu Lys Thr Ile Ser Lys
                325                 330                 335

Ala Lys Gly Gln Pro Arg Glu Pro Gln Val Tyr Thr Leu Pro Pro Cys
                340                 345                 350

Arg Glu Glu Met Thr Lys Asn Gln Val Ser Leu Trp Cys Leu Val Lys
                355                 360                 365

Gly Phe Tyr Pro Ser Asp Ile Ala Val Glu Trp Glu Ser Asn Gly Gln
    370                 375                 380

Pro Glu Asn Asn Tyr Lys Thr Thr Pro Pro Val Leu Asp Ser Asp Gly
385                 390                 395                 400

Ser Phe Phe Leu Tyr Ser Lys Leu Thr Val Asp Lys Ser Arg Trp Gln
                405                 410                 415

Gln Gly Asn Val Phe Ser Cys Ser Val Met His Glu Ala Leu His Asn
                420                 425                 430

His Tyr Thr Gln Lys Ser Leu Ser Leu Ser Pro Gly Lys
        435                 440                 445
```

```
<210> SEQ ID NO 24
<211> LENGTH: 214
<212> TYPE: PRT
<213> ORGANISM: Artificial Sequence
<220> FEATURE:
<223> OTHER INFORMATION: Synthetic Polypeptide

<400> SEQUENCE: 24

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Gly Ser Ser
                20                  25                  30

Leu Thr Trp Leu Gln Gln Lys Pro Gly Lys Ala Pro Lys Arg Leu Ile
            35                  40                  45

Tyr Ala Thr Ser Ser Leu Asp Ser Gly Val Pro Ser Arg Phe Ser Gly
    50                  55                  60

Ser Gly Ser Gly Thr Asp Tyr Thr Leu Thr Ile Ser Ser Leu Gln Pro
65                  70                  75                  80

Glu Asp Phe Ala Thr Tyr Tyr Cys Leu Gln Tyr Ala Ser Ser Pro Tyr
                85                  90                  95

Thr Phe Gly Gln Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205
```

Phe Asn Arg Gly Glu Cys
    210

<210> SEQ ID NO 25
<211> LENGTH: 474
<212> TYPE: PRT
<213> ORGANISM: Artificial Sequence
<220> FEATURE:
<223> OTHER INFORMATION: Synthetic Polypeptide

<400> SEQUENCE: 25

Gln Val Thr Leu Lys Glu Ser Gly Pro Val Leu Val Lys Pro Thr Glu
1               5                   10                  15

Thr Leu Thr Leu Thr Cys Thr Val Ser Gly Phe Ser Leu Thr Asp Tyr
            20                  25                  30

Gly Val Asn Trp Ile Arg Gln Pro Pro Gly Lys Ala Leu Glu Trp Leu
        35                  40                  45

Gly Met Ile Trp Ser Asp Gly Thr Thr Asp Tyr Ser Ser Ala Leu Lys
    50                  55                  60

Ser Arg Leu Thr Ile Ser Lys Asp Thr Ser Lys Ser Gln Val Val Leu
65                  70                  75                  80

Thr Met Thr Asn Met Asp Pro Val Asp Thr Ala Thr Tyr Tyr Cys Ala
                85                  90                  95

Arg Val Asp Gly Tyr Ser His Tyr Tyr Ala Met Asp Tyr Trp Gly Gln
            100                 105                 110

Gly Thr Leu Val Thr Val Ser Ser Gly Gly Gly Gly Ser Gly Gly Gly
        115                 120                 125

Gly Ser Gly Gly Gly Gly Ser Asp Ile Gln Met Thr Gln Ser Pro Ser
    130                 135                 140

Ser Leu Ser Ala Ser Val Gly Asp Arg Val Thr Ile Thr Cys Arg Ala
145                 150                 155                 160

Ser Glu Asn Ile Tyr Ser Tyr Leu Ala Trp Tyr Gln Gln Lys Gln Gly
                165                 170                 175

Lys Ala Pro Gln Leu Leu Ile Tyr Asn Ala Lys Thr Leu Ala Glu Gly
            180                 185                 190

Val Ser Ser Arg Phe Ser Gly Ser Gly Ser Gly Thr Gln Phe Thr Leu
        195                 200                 205

Thr Ile Ser Ser Leu Gln Pro Glu Asp Phe Ala Thr Tyr Tyr Cys Gln
    210                 215                 220

His His Tyr Gly Leu Pro Phe Thr Phe Gly Gln Gly Thr Lys Leu Glu
225                 230                 235                 240

Ile Lys Glu Pro Lys Ser Ser Asp Lys Thr His Thr Cys Pro Pro Cys
                245                 250                 255

Pro Ala Pro Glu Leu Leu Gly Gly Pro Ser Val Phe Leu Phe Pro Pro
            260                 265                 270

Lys Pro Lys Asp Thr Leu Met Ile Ser Arg Thr Pro Glu Val Thr Cys
            275                 280                 285

Val Val Val Asp Val Ser Gln Glu Asp Pro Glu Val Gln Phe Asn Trp
        290                 295                 300

Tyr Val Asp Gly Val Glu Val His Asn Ala Lys Thr Lys Pro Arg Glu
305                 310                 315                 320

Glu Gln Tyr Asn Ser Thr Tyr Arg Val Val Ser Val Leu Thr Val Leu
                325                 330                 335

His Gln Asp Trp Leu Asn Gly Lys Glu Tyr Lys Cys Lys Val Ser Asn
            340                 345                 350

-continued

```
Lys Ala Leu Pro Ala Pro Ile Glu Lys Thr Ile Ser Lys Ala Lys Gly
        355             360             365

Gln Pro Arg Glu Pro Gln Val Cys Thr Leu Pro Pro Ser Gln Glu Glu
        370             375             380

Met Thr Lys Asn Gln Val Ser Leu Ser Cys Ala Val Lys Gly Phe Tyr
385             390             395             400

Pro Ser Asp Ile Ala Val Glu Trp Glu Ser Asn Gly Gln Pro Glu Asn
            405             410             415

Asn Tyr Lys Thr Thr Pro Pro Val Leu Asp Ser Asp Gly Ser Phe Phe
            420             425             430

Leu Val Ser Lys Leu Thr Val Asp Lys Ser Arg Trp Gln Glu Gly Asn
        435             440             445

Val Phe Ser Cys Ser Val Met His Glu Ala Leu His Asn His Tyr Thr
        450             455             460

Gln Lys Ser Leu Ser Leu Ser Pro Gly Lys
465             470
```

```
<210> SEQ ID NO 26
<211> LENGTH: 451
<212> TYPE: PRT
<213> ORGANISM: Artificial Sequence
<220> FEATURE:
<223> OTHER INFORMATION: Synthetic Polypeptide

<400> SEQUENCE: 26

Lys Asn Leu Asp Ala Trp Val Asp Asn Glu Glu Asp Ile Asp Val Ile
1               5               10              15

Leu Lys Lys Ser Thr Ile Leu Asn Leu Asp Ile Asn Asn Asp Ile Ile
            20              25              30

Ser Asp Ile Ser Gly Phe Asn Ser Ser Val Ile Thr Tyr Pro Asp Ala
        35              40              45

Gln Leu Val Pro Gly Ile Asn Gly Lys Ala Ile His Leu Val Asn Asn
        50              55              60

Glu Ser Ser Glu Val Ile Val His Lys Ala Met Asp Ile Glu Tyr Asn
65              70              75              80

Asp Met Phe Asn Asn Phe Thr Val Ser Phe Trp Leu Arg Val Pro Lys
                85              90              95

Val Ser Ala Ser His Leu Glu Gln Tyr Gly Thr Asn Glu Tyr Ser Ile
            100             105             110

Ile Ser Ser Met Lys Lys His Ser Leu Ser Ile Gly Ser Gly Trp Ser
        115             120             125

Val Ser Leu Lys Gly Asn Asn Leu Ile Trp Thr Leu Lys Asp Ser Ala
        130             135             140

Gly Glu Val Arg Gln Ile Thr Phe Arg Asp Leu Pro Asp Lys Phe Asn
145             150             155             160

Ala Tyr Leu Ala Asn Lys Trp Val Phe Ile Thr Ile Thr Asn Asp Arg
            165             170             175

Leu Ser Ser Ala Asn Leu Tyr Ile Asn Gly Val Leu Met Gly Ser Ala
            180             185             190

Glu Ile Thr Gly Leu Gly Ala Ile Arg Glu Asp Asn Asn Ile Thr Leu
        195             200             205

Lys Leu Asp Arg Cys Asn Asn Asn Asn Gln Tyr Val Ser Ile Asp Lys
        210             215             220

Phe Arg Ile Phe Cys Lys Ala Leu Asn Pro Lys Glu Ile Glu Lys Leu
225             230             235             240
```

-continued

```
Tyr Thr Ser Tyr Leu Ser Ile Thr Phe Leu Arg Asp Phe Trp Gly Asn
                245             250             255

Pro Leu Arg Tyr Asp Thr Glu Tyr Tyr Leu Ile Pro Val Ala Ser Ser
                260             265             270

Ser Lys Asp Val Gln Leu Lys Asn Ile Thr Asp Tyr Met Tyr Leu Thr
                275             280             285

Asn Ala Pro Ser Tyr Thr Asn Gly Lys Leu Asn Ile Tyr Tyr Arg Arg
    290             295             300

Leu Tyr Asn Gly Leu Lys Phe Ile Ile Lys Arg Tyr Thr Pro Asn Asn
305             310             315             320

Glu Ile Asp Ser Phe Val Lys Ser Gly Asp Phe Ile Lys Leu Tyr Val
                325             330             335

Ser Tyr Asn Asn Asn Glu His Ile Val Gly Tyr Pro Lys Asp Gly Asn
                340             345             350

Ala Phe Asn Asn Leu Asp Arg Ile Leu Arg Val Gly Tyr Asn Ala Pro
                355             360             365

Gly Ile Pro Leu Tyr Lys Lys Met Glu Ala Val Lys Leu Arg Asp Leu
    370             375             380

Lys Thr Tyr Ser Val Gln Leu Lys Leu Tyr Asp Asp Lys Asn Ala Ser
385             390             395             400

Leu Gly Leu Val Gly Thr His Asn Gly Gln Ile Gly Asn Asp Pro Asn
                405             410             415

Arg Asp Ile Leu Ile Ala Ser Asn Trp Tyr Phe Asn His Leu Lys Asp
                420             425             430

Lys Ile Leu Gly Cys Asp Trp Tyr Phe Val Pro Thr Asp Glu Gly Trp
    435             440             445

Thr Asn Asp
    450
```

```
<210> SEQ ID NO 27
<211> LENGTH: 6
<212> TYPE: PRT
<213> ORGANISM: Artificial Sequence
<220> FEATURE:
<223> OTHER INFORMATION: Synthetic Polypeptide

<400> SEQUENCE: 27

His His His His His His
1               5
```

```
<210> SEQ ID NO 28
<211> LENGTH: 330
<212> TYPE: PRT
<213> ORGANISM: Homo sapiens

<400> SEQUENCE: 28

Ala Ser Thr Lys Gly Pro Ser Val Phe Pro Leu Ala Pro Ser Ser Lys
1               5               10              15

Ser Thr Ser Gly Gly Thr Ala Ala Leu Gly Cys Leu Val Lys Asp Tyr
                20              25              30

Phe Pro Glu Pro Val Thr Val Ser Trp Asn Ser Gly Ala Leu Thr Ser
                35              40              45

Gly Val His Thr Phe Pro Ala Val Leu Gln Ser Ser Gly Leu Tyr Ser
    50              55              60

Leu Ser Ser Val Val Thr Val Pro Ser Ser Ser Leu Gly Thr Gln Thr
65              70              75              80

Tyr Ile Cys Asn Val Asn His Lys Pro Ser Asn Thr Lys Val Asp Lys
```

-continued

```
                85                    90                    95

Arg Val Glu Pro Lys Ser Cys Asp Lys Thr His Thr Cys Pro Pro Cys
            100                   105                   110

Pro Ala Pro Glu Leu Leu Gly Gly Pro Ser Val Phe Leu Phe Pro Pro
            115                   120                   125

Lys Pro Lys Asp Thr Leu Met Ile Ser Arg Thr Pro Glu Val Thr Cys
    130                   135                   140

Val Val Val Asp Val Ser His Glu Asp Pro Glu Val Lys Phe Asn Trp
145                   150                   155                   160

Tyr Val Asp Gly Val Glu Val His Asn Ala Lys Thr Lys Pro Arg Glu
                165                   170                   175

Glu Gln Tyr Asn Ser Thr Tyr Arg Val Val Ser Val Leu Thr Val Leu
                180                   185                   190

His Gln Asp Trp Leu Asn Gly Lys Glu Tyr Lys Cys Lys Val Ser Asn
                195                   200                   205

Lys Ala Leu Pro Ala Pro Ile Glu Lys Thr Ile Ser Lys Ala Lys Gly
    210                   215                   220

Gln Pro Arg Glu Pro Gln Val Tyr Thr Leu Pro Pro Ser Arg Glu Glu
225                   230                   235                   240

Met Thr Lys Asn Gln Val Ser Leu Thr Cys Leu Val Lys Gly Phe Tyr
                245                   250                   255

Pro Ser Asp Ile Ala Val Glu Trp Glu Ser Asn Gly Gln Pro Glu Asn
                260                   265                   270

Asn Tyr Lys Thr Thr Pro Pro Val Leu Asp Ser Asp Gly Ser Phe Phe
                275                   280                   285

Leu Tyr Ser Lys Leu Thr Val Asp Lys Ser Arg Trp Gln Gln Gly Asn
    290                   295                   300

Val Phe Ser Cys Ser Val Met His Glu Ala Leu His Asn His Tyr Thr
305                   310                   315                   320

Gln Lys Ser Leu Ser Leu Ser Pro Gly Lys
                325                   330

<210> SEQ ID NO 29
<211> LENGTH: 330
<212> TYPE: PRT
<213> ORGANISM: Mus musculus

<400> SEQUENCE: 29

Ala Lys Thr Thr Ala Pro Ser Val Tyr Pro Leu Ala Pro Val Cys Gly
1               5                     10                    15

Asp Thr Thr Gly Ser Ser Val Thr Leu Gly Cys Leu Val Lys Gly Tyr
                20                    25                    30

Phe Pro Glu Pro Val Thr Leu Thr Trp Asn Ser Gly Ser Leu Ser Ser
            35                    40                    45

Gly Val His Thr Phe Pro Ala Val Leu Gln Ser Asp Leu Tyr Thr Leu
    50                    55                    60

Ser Ser Ser Val Thr Val Thr Ser Ser Thr Trp Pro Ser Gln Ser Ile
65                    70                    75                    80

Thr Cys Asn Val Ala His Pro Ala Ser Ser Thr Lys Val Asp Lys Lys
                85                    90                    95

Ile Glu Pro Arg Gly Pro Thr Ile Lys Pro Cys Pro Pro Cys Lys Cys
            100                   105                   110

Pro Ala Pro Asn Leu Leu Gly Gly Pro Ser Val Phe Ile Phe Pro Pro
            115                   120                   125
```

-continued

```
Lys Ile Lys Asp Val Leu Met Ile Ser Leu Ser Pro Ile Val Thr Cys
    130                 135                 140

Val Val Val Asp Val Ser Glu Asp Asp Pro Asp Val Gln Ile Ser Trp
145                 150                 155                 160

Phe Val Asn Asn Val Glu Val His Thr Ala Gln Thr Gln Thr His Arg
                165                 170                 175

Glu Asp Tyr Asn Ser Thr Leu Arg Val Val Ser Ala Leu Pro Ile Gln
            180                 185                 190

His Gln Asp Trp Met Ser Gly Lys Glu Phe Lys Cys Lys Val Asn Asn
        195                 200                 205

Lys Asp Leu Pro Ala Pro Ile Glu Arg Thr Ile Ser Lys Pro Lys Gly
    210                 215                 220

Ser Val Arg Ala Pro Gln Val Tyr Val Leu Pro Pro Glu Glu Glu
225                 230                 235                 240

Met Thr Lys Lys Gln Val Thr Leu Thr Cys Met Val Thr Asp Phe Met
                245                 250                 255

Pro Glu Asp Ile Tyr Val Glu Trp Thr Asn Asn Gly Lys Thr Glu Leu
            260                 265                 270

Asn Tyr Lys Asn Thr Glu Pro Val Leu Asp Ser Asp Gly Ser Tyr Phe
        275                 280                 285

Met Tyr Ser Lys Leu Arg Val Glu Lys Lys Asn Trp Val Glu Arg Asn
    290                 295                 300

Ser Tyr Ser Cys Ser Val Val His Glu Gly Leu His Asn His His Thr
305                 310                 315                 320

Thr Lys Ser Phe Ser Arg Thr Pro Gly Lys
                325                 330
```

<210> SEQ ID NO 30
<211> LENGTH: 330
<212> TYPE: PRT
<213> ORGANISM: Artificial Sequence
<220> FEATURE:
<223> OTHER INFORMATION: Synthetic Polypeptide

<400> SEQUENCE: 30

```
Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160
```

-continued

```
Tyr Val Asp Gly Val Glu Val His Asn Ala Lys Thr Lys Pro Arg Glu
                165             170             175

Glu Gln Tyr Asn Ser Thr Tyr Arg Val Val Ser Val Leu Thr Val Leu
            180             185             190

His Gln Asp Trp Leu Asn Gly Lys Glu Tyr Lys Cys Lys Val Ser Asn
            195             200             205

Lys Ala Leu Pro Ala Pro Ile Glu Lys Thr Ile Ser Lys Ala Lys Gly
        210             215             220

Gln Pro Arg Glu Pro Gln Val Cys Thr Leu Pro Pro Ser Arg Glu Glu
225             230             235             240

Met Thr Lys Asn Gln Val Ser Leu Ser Cys Ala Val Lys Gly Phe Tyr
                245             250             255

Pro Ser Asp Ile Ala Val Glu Trp Glu Ser Asn Gly Gln Pro Glu Asn
            260             265             270

Asn Tyr Lys Thr Thr Pro Pro Val Leu Asp Ser Asp Gly Ser Phe Phe
            275             280             285

Leu Val Ser Lys Leu Thr Val Asp Lys Ser Arg Trp Gln Gln Gly Asn
        290             295             300

Val Phe Ser Cys Ser Val Met His Glu Ala Leu His Asn His Tyr Thr
305             310             315             320

Gln Lys Ser Leu Ser Leu Ser Pro Gly Lys
                325             330
```

```
<210> SEQ ID NO 31
<211> LENGTH: 330
<212> TYPE: PRT
<213> ORGANISM: Artificial Sequence
<220> FEATURE:
<223> OTHER INFORMATION: Synthetic Polypeptide

<400> SEQUENCE: 31
```

```
Ala Ser Thr Lys Gly Pro Ser Val Phe Pro Leu Ala Pro Ser Ser Lys
1               5               10              15

Ser Thr Ser Gly Gly Thr Ala Ala Leu Gly Cys Leu Val Lys Asp Tyr
            20              25              30

Phe Pro Glu Pro Val Thr Val Ser Trp Asn Ser Gly Ala Leu Thr Ser
            35              40              45

Gly Val His Thr Phe Pro Ala Val Leu Gln Ser Ser Gly Leu Tyr Ser
        50              55              60

Leu Ser Ser Val Val Thr Val Pro Ser Ser Ser Leu Gly Thr Gln Thr
65              70              75              80

Tyr Ile Cys Asn Val Asn His Lys Pro Ser Asn Thr Lys Val Asp Lys
                85              90              95

Arg Val Glu Pro Lys Ser Cys Asp Lys Thr His Thr Cys Pro Pro Cys
                100             105             110

Pro Ala Pro Glu Leu Leu Gly Gly Pro Ser Val Phe Leu Phe Pro Pro
            115             120             125

Lys Pro Lys Asp Thr Leu Met Ile Ser Arg Thr Pro Glu Val Thr Cys
            130             135             140

Val Val Val Asp Val Ser His Glu Asp Pro Glu Val Lys Phe Asn Trp
145             150             155             160

Tyr Val Asp Gly Val Glu Val His Asn Ala Lys Thr Lys Pro Arg Glu
                165             170             175

Glu Gln Tyr Asn Ser Thr Tyr Arg Val Val Ser Val Leu Thr Val Leu
            180             185             190
```

-continued

```
His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
        210                 215                 220

Gln Pro Arg Glu Pro Gln Val Tyr Thr Leu Pro Pro Cys Arg Glu Glu
225                 230                 235                 240

Met Thr Lys Asn Gln Val Ser Leu Trp Cys Leu Val Lys Gly Phe Tyr
                245                 250                 255

Pro Ser Asp Ile Ala Val Glu Trp Glu Ser Asn Gly Gln Pro Glu Asn
                260                 265                 270

Asn Tyr Lys Thr Thr Pro Pro Val Leu Asp Ser Asp Gly Ser Phe Phe
                275                 280                 285

Leu Tyr Ser Lys Leu Thr Val Asp Lys Ser Arg Trp Gln Gln Gly Asn
        290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 32
<211> LENGTH: 330
<212> TYPE: PRT
<213> ORGANISM: Artificial Sequence
<220> FEATURE:
<223> OTHER INFORMATION: Synthetic Polypeptide

<400> SEQUENCE: 32

Ala Lys Thr Thr Ala Pro Ser Val Tyr Pro Leu Ala Pro Val Cys Gly
1               5                   10                  15

Asp Thr Thr Gly Ser Ser Val Thr Leu Gly Cys Leu Val Lys Gly Tyr
                20                  25                  30

Phe Pro Glu Pro Val Thr Leu Thr Trp Asn Ser Gly Ser Leu Ser Ser
        35                  40                  45

Gly Val His Thr Phe Pro Ala Val Leu Gln Ser Asp Leu Tyr Thr Leu
        50                  55                  60

Ser Ser Ser Val Thr Val Thr Ser Ser Thr Trp Pro Ser Gln Ser Ile
65                  70                  75                  80

Thr Cys Asn Val Ala His Pro Ala Ser Ser Thr Lys Val Asp Lys Lys
                85                  90                  95

Ile Glu Pro Arg Gly Pro Thr Ile Lys Pro Cys Pro Pro Cys Lys Cys
                100                 105                 110

Pro Ala Pro Asn Leu Leu Gly Gly Pro Ser Val Phe Ile Phe Pro Pro
        115                 120                 125

Lys Ile Lys Asp Val Leu Met Ile Ser Leu Ser Pro Ile Val Thr Cys
        130                 135                 140

Val Val Val Asp Val Ser Glu Asp Asp Pro Asp Val Gln Ile Ser Trp
145                 150                 155                 160

Phe Val Asn Asn Val Glu Val His Thr Ala Gln Thr Gln Thr His Arg
                165                 170                 175

Glu Asp Tyr Asn Ser Thr Leu Arg Val Val Ser Ala Leu Pro Ile Gln
                180                 185                 190

His Gln Asp Trp Met Ser Gly Lys Glu Phe Lys Cys Lys Val Asn Asn
        195                 200                 205

Lys Asp Leu Pro Ala Pro Ile Glu Arg Thr Ile Ser Lys Pro Lys Gly
        210                 215                 220
```

-continued

```
Ser Val Arg Ala Pro Gln Val Cys Val Leu Pro Pro Glu Glu Glu
225             230             235             240

Met Thr Lys Lys Gln Val Thr Leu Ser Cys Ala Val Thr Asp Phe Met
            245             250             255

Pro Glu Asp Ile Tyr Val Glu Trp Thr Asn Asn Gly Lys Thr Glu Leu
            260             265             270

Asn Tyr Lys Asn Thr Glu Pro Val Leu Asp Ser Asp Gly Ser Tyr Phe
        275             280             285

Met Val Ser Lys Leu Arg Val Glu Lys Lys Asn Trp Val Glu Arg Asn
    290             295             300

Ser Tyr Ser Cys Ser Val Val His Glu Gly Leu His Asn His His Thr
305             310             315             320

Thr Lys Ser Phe Ser Arg Thr Pro Gly Lys
                325             330

<210> SEQ ID NO 33
<211> LENGTH: 330
<212> TYPE: PRT
<213> ORGANISM: Artificial Sequence
<220> FEATURE:
<223> OTHER INFORMATION: Synthetic Polypeptide

<400> SEQUENCE: 33

Ala Lys Thr Thr Ala Pro Ser Val Tyr Pro Leu Ala Pro Val Cys Gly
1               5               10              15

Asp Thr Thr Gly Ser Ser Val Thr Leu Gly Cys Leu Val Lys Gly Tyr
            20              25              30

Phe Pro Glu Pro Val Thr Leu Thr Trp Asn Ser Gly Ser Leu Ser Ser
        35              40              45

Gly Val His Thr Phe Pro Ala Val Leu Gln Ser Asp Leu Tyr Thr Leu
    50              55              60

Ser Ser Ser Val Thr Val Thr Ser Ser Thr Trp Pro Ser Gln Ser Ile
65              70              75              80

Thr Cys Asn Val Ala His Pro Ala Ser Ser Thr Lys Val Asp Lys Lys
            85              90              95

Ile Glu Pro Arg Gly Pro Thr Ile Lys Pro Cys Pro Pro Cys Lys Cys
        100             105             110

Pro Ala Pro Asn Leu Leu Gly Gly Pro Ser Val Phe Ile Phe Pro Pro
    115             120             125

Lys Ile Lys Asp Val Leu Met Ile Ser Leu Ser Pro Ile Val Thr Cys
    130             135             140

Val Val Val Asp Val Ser Glu Asp Asp Pro Asp Val Gln Ile Ser Trp
145             150             155             160

Phe Val Asn Asn Val Glu Val His Thr Ala Gln Thr Gln Thr His Arg
            165             170             175

Glu Asp Tyr Asn Ser Thr Leu Arg Val Val Ser Ala Leu Pro Ile Gln
            180             185             190

His Gln Asp Trp Met Ser Gly Lys Glu Phe Lys Cys Lys Val Asn Asn
        195             200             205

Lys Asp Leu Pro Ala Pro Ile Glu Arg Thr Ile Ser Lys Pro Lys Gly
    210             215             220

Ser Val Arg Ala Pro Gln Val Tyr Val Leu Pro Pro Cys Glu Glu Glu
225             230             235             240

Met Thr Lys Lys Gln Val Thr Leu Trp Cys Met Val Thr Asp Phe Met
            245             250             255
```

```
Pro Glu Asp Ile Tyr Val Glu Trp Thr Asn Asn Gly Lys Thr Glu Leu
            260                 265                 270

Asn Tyr Lys Asn Thr Glu Pro Val Leu Asp Ser Asp Gly Ser Tyr Phe
            275                 280                 285

Met Tyr Ser Lys Leu Arg Val Glu Lys Lys Asn Trp Val Glu Arg Asn
            290                 295                 300

Ser Tyr Ser Cys Ser Val Val His Glu Gly Leu His Asn His His Thr
305                 310                 315                 320

Thr Lys Ser Phe Ser Arg Thr Pro Gly Lys
                325                 330

<210> SEQ ID NO 34
<211> LENGTH: 107
<212> TYPE: PRT
<213> ORGANISM: Homo sapiens

<400> SEQUENCE: 34

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
            35                  40                  45

Ser Gly Asn Ser Gln Glu Ser Val Thr Glu Gln Asp Ser Lys Asp Ser
            50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105

<210> SEQ ID NO 35
<211> LENGTH: 106
<212> TYPE: PRT
<213> ORGANISM: Homo sapiens

<400> SEQUENCE: 35

Gly Gln Pro Lys Ala Ala Pro Ser Val Thr Leu Phe Pro Pro Ser Ser
1               5                   10                  15

Glu Glu Leu Gln Ala Asn Lys Ala Thr Leu Val Cys Leu Ile Ser Asp
            20                  25                  30

Phe Tyr Pro Gly Ala Val Thr Val Ala Trp Lys Ala Asp Ser Ser Pro
            35                  40                  45

Val Lys Ala Gly Val Glu Thr Thr Thr Pro Ser Lys Gln Ser Asn Asn
            50                  55                  60

Lys Tyr Ala Ala Ser Ser Tyr Leu Ser Leu Thr Pro Glu Gln Trp Lys
65                  70                  75                  80

Ser His Arg Ser Tyr Ser Cys Gln Val Thr His Glu Gly Ser Thr Val
                85                  90                  95

Glu Lys Thr Val Ala Pro Thr Glu Cys Ser
            100                 105

<210> SEQ ID NO 36
<211> LENGTH: 107
<212> TYPE: PRT
<213> ORGANISM: Mus musculus
```

-continued

```
<400> SEQUENCE: 36

Arg Ala Asp Ala Ala Pro Thr Val Ser Ile Phe Pro Pro Ser Ser Glu
1               5                   10                  15

Gln Leu Thr Ser Gly Gly Ala Ser Val Val Cys Phe Leu Asn Asn Phe
            20                  25                  30

Tyr Pro Lys Asp Ile Asn Val Lys Trp Lys Ile Asp Gly Ser Glu Arg
        35                  40                  45

Gln Asn Gly Val Leu Asn Ser Trp Thr Asp Gln Asp Ser Lys Asp Ser
    50                  55                  60

Thr Tyr Ser Met Ser Ser Thr Leu Thr Leu Thr Lys Asp Glu Tyr Glu
65                  70                  75                  80

Arg His Asn Ser Tyr Thr Cys Glu Ala Thr His Lys Thr Ser Thr Ser
                85                  90                  95

Pro Ile Val Lys Ser Phe Asn Arg Asn Glu Cys
            100                 105

<210> SEQ ID NO 37
<211> LENGTH: 106
<212> TYPE: PRT
<213> ORGANISM: Mus musculus

<400> SEQUENCE: 37

Gly Gln Pro Lys Ser Ser Pro Ser Val Thr Leu Phe Pro Pro Ser Ser
1               5                   10                  15

Glu Glu Leu Glu Thr Asn Lys Ala Thr Leu Val Cys Thr Ile Thr Asp
            20                  25                  30

Phe Tyr Pro Gly Val Val Thr Val Asp Trp Lys Val Asp Gly Thr Pro
        35                  40                  45

Val Thr Gln Gly Met Glu Thr Thr Gln Pro Ser Lys Gln Ser Asn Asn
    50                  55                  60

Lys Tyr Met Ala Ser Ser Tyr Leu Thr Leu Thr Ala Arg Ala Trp Glu
65                  70                  75                  80

Arg His Ser Ser Tyr Ser Cys Gln Val Thr His Glu Gly His Thr Val
                85                  90                  95

Glu Lys Ser Leu Ser Arg Ala Asp Cys Ser
            100                 105

<210> SEQ ID NO 38
<211> LENGTH: 19
<212> TYPE: DNA
<213> ORGANISM: Artificial Sequence
<220> FEATURE:
<223> OTHER INFORMATION: Synthetic Polynucleotide

<400> SEQUENCE: 38
tgcatttgaa ctccttgcc                                                    19

<210> SEQ ID NO 39
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 39
ccatcaatct tccacttgac                                                   20

<210> SEQ ID NO 40
<211> LENGTH: 232
```

```
<212> TYPE: PRT
<213> ORGANISM: Artificial Sequence
<220> FEATURE:
<223> OTHER INFORMATION: Synthetic Polypeptide

<400> SEQUENCE: 40

Glu Pro Lys Ser Cys Asp Lys Thr His Thr Cys Pro Pro Cys Pro Ala
1               5                   10                  15

Pro Glu Leu Leu Gly Gly Pro Ser Val Phe Leu Phe Pro Pro Lys Pro
                20                  25                  30

Lys Asp Thr Leu Met Ile Ser Arg Thr Pro Glu Val Thr Cys Val Val
            35                  40                  45

Val Asp Val Ser His Glu Asp Pro Glu Val Lys Phe Asn Trp Tyr Val
        50                  55                  60

Asp Gly Val Glu Val His Asn Ala Lys Thr Lys Pro Arg Glu Glu Gln
65                  70                  75                  80

Tyr Asn Ser Thr Tyr Arg Val Val Ser Val Leu Thr Val Leu His Gln
                85                  90                  95

Asp Trp Leu Asn Gly Lys Glu Tyr Lys Cys Lys Val Ser Asn Lys Ala
                100                 105                 110

Leu Pro Ala Pro Ile Glu Lys Thr Ile Ser Lys Ala Lys Gly Gln Pro
            115                 120                 125

Arg Glu Pro Gln Val Tyr Thr Leu Pro Pro Cys Arg Glu Glu Met Thr
        130                 135                 140

Lys Asn Gln Val Ser Leu Trp Cys Leu Val Lys Gly Phe Tyr Pro Ser
145                 150                 155                 160

Asp Ile Ala Val Glu Trp Glu Ser Asn Gly Gln Pro Glu Asn Asn Tyr
                165                 170                 175

Lys Thr Thr Pro Pro Val Leu Asp Ser Asp Gly Ser Phe Phe Leu Tyr
                180                 185                 190

Ser Lys Leu Thr Val Asp Lys Ser Arg Trp Gln Gln Gly Asn Val Phe
            195                 200                 205

Ser Cys Ser Val Met His Glu Ala Leu His Asn His Tyr Thr Gln Lys
    210                 215                 220

Ser Leu Ser Leu Ser Pro Gly Lys
225                 230

<210> SEQ ID NO 41
<211> LENGTH: 232
<212> TYPE: PRT
<213> ORGANISM: Artificial Sequence
<220> FEATURE:
<223> OTHER INFORMATION: Synthetic Polypeptide

<400> SEQUENCE: 41

Glu Pro Lys Ser Ser Asp Lys Thr His Thr Cys Pro Pro Cys Pro Ala
1               5                   10                  15

Pro Glu Leu Leu Gly Gly Pro Ser Val Phe Leu Phe Pro Pro Lys Pro
                20                  25                  30

Lys Asp Thr Leu Met Ile Ser Arg Thr Pro Glu Val Thr Cys Val Val
            35                  40                  45

Val Asp Val Ser Gln Glu Asp Pro Glu Val Gln Phe Asn Trp Tyr Val
        50                  55                  60

Asp Gly Val Glu Val His Asn Ala Lys Thr Lys Pro Arg Glu Glu Gln
65                  70                  75                  80

Tyr Asn Ser Thr Tyr Arg Val Val Ser Val Leu Thr Val Leu His Gln
                85                  90                  95
```

-continued

```
Asp Trp Leu Asn Gly Lys Glu Tyr Lys Cys Lys Val Ser Asn Lys Ala
            100             105             110

Leu Pro Ala Pro Ile Glu Lys Thr Ile Ser Lys Ala Lys Gly Gln Pro
        115             120             125

Arg Glu Pro Gln Val Cys Thr Leu Pro Pro Ser Gln Glu Glu Met Thr
    130             135             140

Lys Asn Gln Val Ser Leu Ser Cys Ala Val Lys Gly Phe Tyr Pro Ser
145             150             155             160

Asp Ile Ala Val Glu Trp Glu Ser Asn Gly Gln Pro Glu Asn Asn Tyr
            165             170             175

Lys Thr Thr Pro Pro Val Leu Asp Ser Asp Gly Ser Phe Phe Leu Val
            180             185             190

Ser Lys Leu Thr Val Asp Lys Ser Arg Trp Gln Glu Gly Asn Val Phe
        195             200             205

Ser Cys Ser Val Met His Glu Ala Leu His Asn His Tyr Thr Gln Lys
    210             215             220

Ser Leu Ser Leu Ser Pro Gly Lys
225             230
```